United States Patent
Wang et al.

(10) Patent No.: US 10,330,689 B2
(45) Date of Patent: *Jun. 25, 2019

(54) NEURAL PROTEINS AS BIOMARKERS FOR NERVOUS SYSTEM INJURY AND OTHER NEURAL DISORDERS

(71) Applicants: UNIVERSITY OF FLORIDA RESEARCH FOUNDATION, INC., Gainesville, FL (US); BANYAN BIOMARKERS, INC., San Diego, CA (US)

(72) Inventors: Kevin Ka-Wang Wang, Gainesville, FL (US); Monika Oli, Gainesville, FL (US); Ming-Cheng Liu, Gainesville, FL (US)

(73) Assignees: UNIVERSITY OF FLORIDA RESEARCH FOUNDATION, INC., Gainesville, FL (US); BANYAN BIOMARKERS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,489

(22) Filed: Nov. 3, 2017

(65) Prior Publication Data

US 2018/0059123 A1   Mar. 1, 2018

Related U.S. Application Data

(60) Continuation of application No. 15/340,002, filed on Nov. 1, 2016, now Pat. No. 9,810,698, which is a continuation of application No. 12/950,142, filed on Nov. 19, 2010, now Pat. No. 9,664,694, which is a continuation of application No. 12/822,560, filed on Jun. 24, 2010, now Pat. No. 8,492,107, which is a continuation-in-part of application No. 12/137,194, filed on Jun. 11, 2008, now abandoned, which is a division of application No. 11/107,248, filed on Apr. 15, 2005, now Pat. No. 7,396,654.

(60) Provisional application No. 60/562,944, filed on Apr. 15, 2004.

(51) Int. Cl.
G01N 33/68     (2006.01)
C12Q 1/6883    (2018.01)
C07K 16/18     (2006.01)

(52) U.S. Cl.
CPC ......... *G01N 33/6896* (2013.01); *C07K 16/18* (2013.01); *C12Q 1/6883* (2013.01); *G01N 2800/28* (2013.01); *G01N 2800/52* (2013.01)

(58) Field of Classification Search
CPC ........... A61K 39/395; A61K 39/39541; G01N 33/483; G01N 33/53; G01N 33/6896
See application file for complete search history.

(56) References Cited

U.S. PATENT DOCUMENTS

| | | |
|---|---|---|
| 5,118,606 A | 6/1992 | Lynch et al. |
| 5,231,000 A | 7/1993 | Majocha et al. |
| 5,492,812 A | 2/1996 | Vooheis |
| 6,048,703 A | 4/2000 | Siman et al. |
| 6,589,746 B1 | 7/2003 | Zelman |
| 7,144,708 B2 | 12/2006 | Janigro et al. |
| 7,396,654 B2 | 7/2008 | Hayes et al. |
| 7,456,027 B2 | 11/2008 | Wang et al. |
| 8,298,835 B2 | 10/2012 | Wang et al. |
| 8,492,107 B2 | 7/2013 | Wang et al. |
| 9,810,698 B2 | 11/2017 | Wang et al. |
| 2002/0123059 A1 | 9/2002 | Ho |
| 2003/0040660 A1 | 2/2003 | Jackowski et al. |
| 2003/0119064 A1 | 6/2003 | Valkirs et al. |
| 2003/0199000 A1 | 10/2003 | Valkirs et al. |
| 2004/0121343 A1 | 6/2004 | Buechler et al. |
| 2004/0203083 A1 | 10/2004 | Buechler et al. |
| 2004/0253637 A1 | 12/2004 | Buechler et al. |
| 2005/0260697 A1 | 11/2005 | Wang et al. |
| 2006/0246489 A1 | 11/2006 | Svetlov et al. |
| 2007/0003982 A1 | 1/2007 | Hayes et al. |
| 2007/0042425 A1 | 2/2007 | Hochstrasser et al. |
| 2007/0298433 A1 | 12/2007 | Sia et al. |
| 2009/0087868 A1 | 4/2009 | Wang et al. |
| 2011/0082203 A1 | 4/2011 | Wang et al. |
| 2011/0143375 A1 | 6/2011 | Wang et al. |
| 2011/0177974 A1 | 7/2011 | Wang et al. |
| 2012/0202231 A1 | 8/2012 | Wang et al. |
| 2013/0022982 A1 | 1/2013 | Wang et al. |
| 2013/0029362 A1 | 1/2013 | Jeromin et al. |

(Continued)

FOREIGN PATENT DOCUMENTS

| | | |
|---|---|---|
| EP | 2 143 735 | 1/2010 |
| JP | 2003 070498 | 3/2003 |

(Continued)

OTHER PUBLICATIONS

Van Geel et al., Clinica Chimica Acta, 326:151-154, (Year: 2002).*
Missler et al., Clinical Chemistry, 45(1): 138-141, (Year: 1999).*
Zaffaroni, M. "Biological Indicators of the Neurodegenerative Phase of Multiple Sclerosis", *Neurol Sci*, 2003, pp. S279-S282, vol. 24.
Teunissen, C. E. et al. "Biochemical Markers Related to Alzheimer's Dementia in Serum and Cerebrospinal Fluid", *Neurobiology of Aging*, 2002, pp. 485-508, vol. 23.
Tooney, P. A. et al. "Neurons Expressing Calcium-binding Proteins in the Prefrontal Cortex in Schizophrenia", *Progress in Neuro-Psychopharmacology & Biological Psychiatry*, 2004, pp. 273-278, vol. 28.
Dekosky, S. T. et al. "Looking Backward to Move Forward: Early Detection of Neurodegenerative Disorders", *Science*, Oct. 31, 2003, pp. 830-834, vol. 302.

(Continued)

*Primary Examiner* — Kimberly Ballard
*Assistant Examiner* — Stacey N MacFarlane
(74) *Attorney, Agent, or Firm* — Morrison & Foerster LLP

(57) ABSTRACT

The present invention identifies biomarkers that are diagnostic of nerve cell injury and/or neuronal disorders. Detection of different biomarkers of the invention are also diagnostic of the degree of severity of nerve injury, the cell(s) involved in the injury, and the subcellular localization of the injury.

14 Claims, 15 Drawing Sheets

(56) References Cited

U.S. PATENT DOCUMENTS

| | | | |
|---|---|---|---|
| 2013/0029859 | A1 | 1/2013 | Svetlov et al. |
| 2014/0275294 | A1 | 9/2014 | Svetlov et al. |
| 2014/0303041 | A1 | 10/2014 | Hayes et al. |
| 2014/0342381 | A1 | 11/2014 | Hayes |
| 2015/0141528 | A1 | 5/2015 | Larner |
| 2015/0259740 | A1 | 9/2015 | Pollard et al. |
| 2015/0268252 | A1 | 9/2015 | Svetlov et al. |
| 2017/0146555 | A1 | 5/2017 | Wang et al. |
| 2018/0031577 | A1 | 2/2018 | Wang et al. |

FOREIGN PATENT DOCUMENTS

| | | |
|---|---|---|
| WO | WO 95/26506 | 10/1995 |
| WO | WO-03/016910 | 2/2003 |
| WO | WO 03/019181 | 3/2003 |
| WO | WO 2004/025298 | 3/2004 |
| WO | WO-04/059293 | 7/2004 |
| WO | WO-04/078204 | 9/2004 |
| WO | WO 2005/004794 | 1/2005 |
| WO | WO-05/029087 | 3/2005 |
| WO | WO-05/029088 | 3/2005 |
| WO | WO-05/106038 | 11/2005 |
| WO | WO-05/113798 | 12/2005 |
| WO | WO-07/007129 | 1/2007 |
| WO | WO-07/046811 | 4/2007 |
| WO | WO-07/140188 | 12/2007 |
| WO | WO-10/019553 | 2/2010 |
| WO | WO-10/059242 | 5/2010 |
| WO | WO 2015/157390 | 12/2016 |

OTHER PUBLICATIONS

Cutler, N. R. et al. "Review of the Next Generation of Alzheimer's Disease Therapeutics: Challenges for Drug Development", *Prog. Neuro-Psychopharmacol. & Biol. Psychiat.*, 2001, pp. 27-57, vol. 25.

Blennow, K. "Cerebrospinal Fluid Protein Biomarkers for Alzheimer's Disease", *NeuroRx: The Journal of the American Society for Experimental Neuro Therapeutics*, Apr. 2004, pp. 213-225, vol. 1.

Smith, D. H. et al. "Protein Accumulation in Traumatic Brain Injury", *NeuroMolecular Medicine*, 2003, pp. 59-72, vol. 4.

André, V. M. et al. "NMDA Receptor Alterations in Neurons from Pediatric Cortical Dysplasia Tissue", *Cerebral Cortex*, Jun. 2004, pp. 634-646, vol. 14.

Ohta, M. et al. "Clinical and Analytical Evaluation of an Enzyme Immunoassay for Myelin Basic Protein in Cerebrospinal Fluid", *Clinical Chemistry*, 2000, pp. 1326-1330, vol. 46, No. 9.

Taheri, S. et al. "The Role of Hypocretins (Orexins) in Sleep Regulation and Narcolepsy", *Annu. Rev. Neurosci.*, 2002, pp. 283-313, vol. 25.

Zhang, X. et al. "Phenotypes of T Cells Infiltrating the Eyes in Autoimmune Anterior Uveitis Associated with EAE", *Investigative Ophthalmology & Visual Science*, May 2002, pp. 1499-1508, vol. 43, No. 5.

Everbroeck, B. V. et al. "A Prospective Study of CSF Markers in 250 Patients with Possible Creutzfeldt-Jakob Disease", *J. Neurol Neurosurg Psychiatry*, 2003, pp. 1210-1214, vol. 74.

Inden, M. et al. "Proteasome Inhibitors Protect Against Degeneration of Nigral Dopaminergic Neurons in Hemiparkinsonian Rats", *J Pharmacol Sci*, 2005, pp. 203-211, vol. 97.

Yohrling, G. J. et al. "Inhibition of Tryptophan Hydroxylase Activity and Decreased 5-HT$_{1A}$ Receptor Binding in a Mouse Model of Huntington's Disease", *Journal of Neurochemistry*, 2002, pp. 1416-1423, vol. 82.

Pearl, P. L. et al. "Clinical Aspects of the Disorders of GABA Metabolism in Children", *Curr Opin Neurol*, 2004, pp. 107-113, vol. 17.

Sanchez, J. C. et al. "Cystatin C as a Potential Cerebrospinal Fluid Marker for the Diagnosis of Creutzfeldt-Jakob Disease", *Proteomics*, 2004, pp. 2229-2233, vol. 4.

Wilson, K. E. et al. "Functional Genomics and Proteomics: Application in Neurosciences", *J Neurol Neurosurg Psychiatry*, 2004, pp. 529-538, vol. 75.

Estrov, et al, "Caspase 2 and Caspase 3 Protein Levels as Predictors of Survival in Acute Myelogenous Leukemia", *Blood*, Nov. 1, 1998, pp. 3090-3097, vol. 92, No. 9.

Kadota, Y. et al. "A Newly Identified Membrane Protein Localized Exclusively in Intracellular Organelles of Neurons", *Molecular Brain Research*, 1997, pp. 265-273, vol. 46.

Nakanishi, K. et al. "Molecular Characterization of a Transport Vesicle Protein Neurensin-2, a homologue of Neurensin-1, expressed in neural cells", *Brain Research*, 2006, pp. 1-8, vol. 1081.

Borghi, R. et al. "Full length alpha-synuclein is present in cerebrospinal fluid from Parkinson's disease and normal subjects", *Neuroscience Letters*, 2000, pp. 65-67, vol. 287.

Dambinova, S. et al. "The presence of autoantibodies to N-terminus domain of GluR1 subunit of AMPA receptor in the blood serum of patients with epilepsy", *Journal of Neurological Sciences*, 1997, pp. 93-97, vol. 152.

Dambinova, S. et al. "Blood Test Detecting Autoantibodies to N-Methyl-D-aspartate Neuroreceptors for Evaluation of Patients with Transient Ischemic Attack and Stroke", *Clinical Chemistry*, 2003, pp. 1752-1762, vol. 49, No. 10.

Jakowec, M. et al. "The native form of alpha-synuclein is not found in the cerebrospinal fluid of patients with Parkinson's disease or normal controls", *Neuroscience Letters*, 1998, pp. 13-16, vol. 253.

Posmantur, R. et al. "A calpain inhibitor attenuates cortical cytoskeletal protein loss after experimental traumatic brain injury in the rat", *Neuroscience*, 1997, pp. 875-888, vol. 77, No. 3.

Pike, B. et al. "Accumulation of non-erythroid alpha II-spectrin and calpain-cleaved alpha II-spectrin breakdown products in cerebrospinal fluid after traumatic brain injury in rats", *Journal of Neurochemistry*, 2001, pp. 1297-1306, vol. 78.

Rosengren, L. et al. "Patients with Amyotrophic Lateral Sclerosis and Other Neurodegenerative Diseases Have Increased Levels of Neurofilament Protein in CSF", *Journal of Neurochemistry*, 1996, pp. 2013-2018, vol. 67, No. 5.

Zemlan, F. et al. "Quantification of Axonal Damage in Traumatic Brain Injury: Affinity Purification and Characterization of Cerebrospinal Fluid Tau Proteins", *Journal of Neurochemistry*, 1999, pp. 741-750, vol. 72, No. 2.

Sjogren, M. et al. "Neurofilament Protein in Cerebrospinal Fluid: A Marker of White Matter Changes", 2001, *Journal of Neuroscience Research*, 2001, pp. 510-516, vol. 66.

Shea, T. et al. "Calcium Influx into Human Neuroblastoma Cells Induces ALZ-50 Immunoreactivity: Involvement of Calpain-Mediated Hydrolysis of Protein Kinase C", *Journal of Neurochemistry*, 1996, pp. 1539-1549, vol. 66, No. 4.

Denning, M. et al. "Protein Kinase C delta Is Activated by Capase-dependent Proteolysis during Ultraviolet Radiation-induced Apoptosis of Human Keratinocytes", *The Journal of Biological Chemistry*, 1998, pp. 29995-30002, vol. 273, No. 45.

Koriyama, H. et al. "Proteolytic Activation of Protein Kinase C delta and epsilon by Capase-3 in U937 Cells During Chemotherapeutic Agent-Induced Apoptosis", *Cell Signal*, 1999, pp. 831-838, vol. 11, No. 11.

Schwab, B. L. et al. "Cleavage of plasma membrane calcium pumps by caspases: a link between apoptosis and necrosis", *Cell Death and Differentiation*, 2002, pp. 818-831, vol. 9.

Hajimohammadreza, I. et al. "A Specific Inhibitor of Calcium/Calmodulin-Dependent Protein Kinase-II Provides Neuroprotection Against NMDA- and Hypoxia/Hypoglycemia-Induced Cell Death", *The Journal of Neuroscience*, 1995, pp. 4093-4101, vol. 15, No. 5.

Hajimohammadreza, I. et al. "Neuronal Nitric Oxide Synthase and Calmodulin-Dependent Protein Kinase II alpha Undergo Neurotoxin-Induced Proteolysis", *Journal of Neurochemistry*, 1997, pp. 1006-1013, vol. 69, No. 3.

Toyota, H. et al. "Calpain-induced Bax-clevage product is a more potent inducer of cell death than wild-type Bax", *Cancer Letters*, 2003, pp. 221-230, vol. 189.

McGinnist, K. et al. "Calcium/Calmodulin-dependent Protein Kinase IV Is Cleaved by Caspase-3 and Calpain in SH-SY5Y Human

(56) References Cited

OTHER PUBLICATIONS

Neuroblastoma Cells Undergoing Apoptosis", *The Journal of Biological Chemistry*, 1998, pp. 19993-20000, vol. 273, No. 32.

Cao, X. et al. "Cleavage of Bax to p18 Bax accelerates stress-induced apoptosis, and a cathespin-like protease may rapidly degrade p18 Bax", *Blood*, 2003, pp. 2605-2614, vol. 102, No. 7.

Shigeta, K. et al. "Fragmentation of a 70000-dalton calpastatin molecule upon its complex formation with calpain", *Biochem. Int.*, 1984, pp. 327-333, vol. 9, No. 3.

Mukerjee, N. et al. "Caspase-Mediated Calcineurin Activation Contributes to IL-2 Release during T Cell Activation", 2001, *Biochemical and Biophysical Research Communications*, 2001, pp. 1192-1199, vol. 285, No. 5.

Saido, T.C. et al. "Spatial Resolution of Fodrin Proteolysis in Postischemic Brain", *The Journal of Biological Chemistry*, 1993, pp. 25239-25243, vol. 268, No. 33.

Nath, R. et al. "Non-erythroid α-spectrin breakdown by calpain and interleukin 1β-converting-enzyme-like protease(s) in apoptotic cells: contributory roles of both protease families in neuronal apoptosis", *Biochem. J.*, 1996, pp. 683-690, vol. 319.

Papa, L. et al. "Ubiquitin C-terminal hydrolase is a novel biomarker in humans for server traumatic brain injury", *Crit. Care. Med.*, 2010, pp. 138-144, vol. 38, No. 1, XP-009132536.

Liu, M. C. et al. "Ubiquitin C-terminal hydrolase-L1 as a biomarker for ischemic and traumatic brain injury in rats", *European Journal of Neuroscience*, 2010, pp. 722-732, vol. 31, XP-002579053.

Araki, M. et al. "Developmentally regulated expression of Neuro-p24 and its possible function in neurite extension" *Neuroscience Research*, 2002, pp. 379-389, vol. 44, No. 4.

Hansen, L. A. et al. "Frontal cortical synaptophysin in Lewy body diseases: relation to Alzheimer's disease and dementia" *J. Neurol. Neurosurg Psychiatry*, 1998, pp. 653-656, vol. 64, No. 5, XP-002598264.

Miller, L. P. et al. "Excitatory amino acid receptor subtype binding following traumatic brain injury" *Brain Research*, Aug. 1990, pp. 103-107, vol. 526, No. 1, XP-002598263.

Kronborg, C.S. et al. "Pre-symptomatic increase in urine-orosomucoid excretion in pre-eclamptic women" *Acta Obstetricia et Gynecologica*, 2007, pp. 930-937, vol. 86.

Maynard, S. E. et al. "Excess placental soluble fms-like tyrosine kinase 1 (sFlt1) may contribute to endothelial dysfunction, hypertension, and proteinuria in preeclampsia" *J. Clin. Invest.*, 2003, pp. 649-658, vol. 111, No. 5.

Li, G. L. et al. "Expression of the ubiquitin carboxyl-terminal hydrolase PGP 9.5 in axons following spinal cord compression trauma. An immunohistochemical study in the rat.", *APMIS*, 1997, pp. 384-390, vol. 105.

Yu, W. et al. "Accumulation of immunoreactivity to ubiquitin carboxyl-terminal hydrolase PGP 9.5 in axons of human cases with spinal cord lesions", *APMIS*, 1998, pp. 1081-1087, vol. 106.

Dash, P. et al. "Biomarkers for the Diagnosis, Prognosis, and Evaluation of Treatment Efficacy for Traumatic Brain Injury" *The Journal of the American Society for Experimental NeuroTherapeutics*, Jan. 2010, pp. 100-114, vol. 7.

Liu, Y. et al. "The UCH-L1 Gene Encodes Two Opposing Enzymatic Activities that Affect α-Synuclein Degradation and Parkinson's Disease Susceptibility" *Cell*, Oct. 18, 2002, pp. 209-218, vol. 111.

Cookson, "Parkin's substrates and the pathways leading to neuronal damage," Neuromolecular Med (2003) 3(1):1-13.

Foerch et al., "Serum glial fibrillary acidic protein as a biomarker for intracerebral hemorrhage in patients with acute stroke," J Neurol Neurosurg Psychiatry (2006) 77:181-184.

Herrmann et al., "Release of Glial Tissue-Specific Proteins After Acute Stroke: A comparative analysis of serum concentrations of protein S-100B and glial fibrillary acidic protein," Stroke (2000) 31(11):2670-2677.

International Preliminary Report of Patentability for PCT/US05/12746, dated Dec. 3, 2011, 6 pages.

International Search Report and Written Opinion for PCT/US05/12746, dated Mar. 22, 2007, 9 pages.

Lamers et al., "Protein S-100b, Neuron-Specific Enolase (NSE), Myelin Basic Protein (MBP) and Glial Fibrillary Acidic Protein (GFAP) in Cerebrospinal Fluid (CSF) and Blood of Neurological Patients," Brain Res Bull (2003) 61(3): 261-264.

Lowe et al., "Ubiquitin carboxyl-terminal hydrolase (PGP 9.5) is selectively present in ubiquitinated inclusion bodies characteristic of human neurodegenerative diseases," J Pathol (1990) 161(2):153-160.

Lumpkins et al., "Glial Fibrillary Acidic Protein is Highly Correlated With Brain Injury," J Trauma (2008) 65(4):778-782.

McLendon et al., "Immunohistochemistry of the glial fibrillary acidic protein: basic and applied considerations," Brain Pathol (1994) 4(3):221-228.

Missler et al., "Measurement of Glial Fibrillary Acidic Protein in Human Blood: Analytical Method and Preliminary Clinical Results," Clin Chem (1999) 45(1):138-141.

Nylen et al., "Increased serum-GFAP in patients with severe traumatic brain injury is related to outcome," J Neurol Sci (2006) 240(1-2):85-91.

Papa et al., "Use of biomarkers for diagnosis and management of traumatic brain injury patients," Expert Opin. Med. Diagn (2008) 2(8):937-945.

Pelinka et al., "Glial Fibrillary Acidic Protein in Serum After Traumatic Brain Injury and Multiple Trauma," J Trauma (2004) 57(5):1006-1012.

Poletaev et al., "Serum anti-S100b, anti-GFAP and anti-NGF autoantibodies of IgG class in healthy persons and patients with mental and neurological disorders," Autoimmunity (2000) 32(1):33-38.

Towern et al., "Detection of neuron-specific protein gene product (PGP) 9.5 in the rat and zebrafish using anti-human PGP9.5 antibodies," Neurosci Lett (1996) 210(1)21-24.

Van Geel et al., "Measurement of glial fibrillary acidic protein in blood: an analytical method," Clin Chim Acta (2002) 326(1-2):151-154.

Vissers et al., "Rapid immunoassay for the determination of glial fibrillary acidic protein (GFAP) in serum," Clin Chim Acta (2006) 366(1-2):336-340.

Vos et al., "Glial and neuronal proteins in serum predict outcome after severe traumatic brain injury," Neurology (2004) 62(8):1303-1310.

Pekny, M. et al. "The Role of Astrocytes and Complement System in Neural Plasticity" *International Review of Neurobiology*, 2007, pp. 95-111, vol. 82.

Pelinka, L. E. et al. "GFAP Versus S100B in Serum after Traumatic Brain Injury: Relationship to Brian Damage and Outcome" *Journal of Neurotrauma*, 2004, pp. 1553-1561, vol. 21, No. 11.

Urrea, C. et al. "Widespread cellular proliferation and focal neurogenesis after traumatic brain injury in the rat" *Restorative Neurology and Neuroscience*, 2007, pp. 65-76, vol. 25.

Vos, P. E. et al. "Increased GFAP and S100β but not NSE serum levels after subarachnoid haemorrhage are associated with clinical severity" *European Journal of Neurology*, 2006, pp. 632-638, vol. 13, No. 6.

Wang, K. K. W. et al. "Proteomic identification of biomarkers of traumatic brain injury" *Expert Review of Proteomics*, 2005, pp. 603-614, vol. 2, No. 4.

Xu, Q. G. et al. "Facilitated Sprouting in a Peripheral Nerve Injury" *Neuroscience*, 2008, pp. 877-887, vol. 152.

U.S. Appl. No. 15/308,934, filed Nov. 4, 2016.

"Cerebral contusion" published by Wikipedia online on Sep. 13, 2006. Retrieved from http://en.wikipedia.org/wik/Cerebral_contusion. Retrieved on Mar. 20, 2017 1:54:09 PM.

Hinkle et al., "GFAP and S100β Expression in the Cortex and Hippocampus in Response to Mild Cortical Contusion," J Neurotrama (1997) 14(10):729-738.

Lewis, L. et al. "Utility of Serum Biomarkers in the Diagnosis and Stratification of Mild Traumatic Brain Injury" *Academic Emergency Medicine*, Jun. 2017, pp. 710-720, vol. 24, No. 6.

Esselman, P.C. et al. "Review of subject; Classification of the spectrum of mild traumatic brain injury" *Brain Injury*, 1995, pp. 417-424, vol. 9, No. 4.

(56) References Cited

OTHER PUBLICATIONS

Villines, Z. "Contusion vs. Concussion: Understanding the Difference" *Spinal Cord Injury Journal*, Nov. 23, 2015, retrieved from the internet https://web-beta.archive.org/we/20151202013742/http://www.spinalcord.com/blog/contusion-vs.-concussion-understanding-the-difference, retrieved on May 4, 2017.
Baldwin, S. A. et al. "Intermediate filament change in astrocytes following mild cortical contusion" *Glia*, Mar. 1996, pp. 266-275, vol. 16, No. 3.
Nawashiro, H. et al. "Selective vulnerability of hippocampal CA3 neurons to hypoxia after mild concussion in the rat" *Neurological Research*, 1995, pp. 455-460, vol. 17, No. 6.
Mao, Q. et al. "The value of serum myelin basic protein in assessment of severity of acute closed head trauma" *Hua Xi Yi Ke Da Xue Xue Bao*, Jun. 1995, pp. 135-137, vol. 26, No. 2.
Wang, H. et al. "A study of HSP70 and NF in brain contusion timing" *Fa Yi Xue Za Zhi*, Aug. 2000, pp. 132-134, vol. 16, No. 3.
Petricoin, E. F. et al. "Clinical proteomics: translating benchside promise into bedside reality" *Nature Reviews*, 2002, pp. 683-695, vol. 1.
Petzold, A. et al. "An ELISA for glial fibrillary acidic protein" *J Immunol Methods*, 2004, pp. 169-177, vol. 287, Nos. 1-2.
U.S. Appl. No. 15/441,183, filed Feb. 23, 2017, by Svetlov et al.

\* cited by examiner

1: h TBI CSF (7.5 uL)
2: h TBI Serum 200 ul ( MWkDa cut off)
3: h TBI Serum (175 ul) + human CSF (25 ul) (30-50 kDa cut off)
4: Serum (10-30 kDa cut off)
5: Serum+ CSF (10-30 kDa cut off)

NEURAL PROTEINS AS BIOMARKERS FOR NERVOUS SYSTEM INJURY AND OTHER NEURAL DISORDERS

CROSS-REFERENCE TO RELATED APPLICATIONS

This application is a continuation of U.S. Ser. No. 15/340,002, filed Nov. 1, 2016, now U.S. Pat. No. 9,810,698, which is a continuation of U.S. Ser. No. 12/950,142, filed Nov. 19, 2010, now U.S. Pat. No. 9,664,694, which is a continuation of U.S. Ser. No. 12/822,560, filed Jun. 24, 2010, now U.S. Pat. No. 8,492,107, which is a continuation-in-part of U.S. Ser. No. 12/137,194, filed Jun. 11, 2008, now abandoned, which is a divisional of U.S. Ser. No. 11/107,248, filed Apr. 15, 2005, now U.S. Pat. No. 7,396,654, which claims the benefit of U.S. Provisional Application Ser. No. 60/562,944, filed Apr. 15, 2004, the disclosures of which are hereby incorporated by reference in their entirety, including all figures, tables and amino acid or nucleic acid sequences.

The invention was made with government support under Grant NS039091 awarded by the National Institutes of Health and Grant NS040182 awarded by the National Institutes of Health and Grants DAMD 17-99-1-9565 and DAMD 17-01-1-0765 awarded by the United States Army. The government has certain rights in the invention.

FIELD OF THE INVENTION

The invention provides for the reliable detection and identification of biomarkers, important for the diagnosis and prognosis of damage to the nervous system (central nervous system (CNS) and peripheral nervous system (PNS)), brain injury and neural disorders. The protein/peptide profile in patients with damage to nerves and brain cells are distinguished from normal individuals using inexpensive techniques. These techniques provide simple yet sensitive approaches to diagnosing damage to the central nervous system, brain injury and neuronal disorders using biological fluids.

BACKGROUND OF THE INVENTION

The incidence of traumatic brain injury (TBI) in the United States is conservatively estimated to be more than 2 million persons annually with approximately 500,000 hospitalizations. Of these, about 70,000 to 90,000 head injury survivors are permanently disabled. The annual economic cost to society for care of head-injured patients is estimated at $25 billion. These figures are for the civilian population only and the incidence is much greater when combat casualties are included. In modern warfare (1993-2000), TBI is the leading cause of death (53%) among wounded who have reached medical care facilities.

Assessment of pathology and neurological impairment immediately after TBI is crucial for determination of appropriate clinical management and for predicting long-term outcome. The outcome measures most often used in head injuries are the Glasgow Coma Scale (GCS), the Glasgow Outcome Scale (GOS), computed tomography, and magnetic resonance imaging (Mill) to detect intracranial pathology. However, despite dramatically improved emergency triage systems based on these outcome measures, most TBI suffer long term impairment and a large number of TBI survivors are severely affected despite predictions of "good recovery" on the GOS. In addition, CT and MM are expensive and cannot be rapidly employed in an emergency room environment. Moreover, in austere medical environments associated with combat, accurate diagnosis of TBI would be an essential prerequisite for appropriate triage of casualties.

The mammalian nervous system comprises a peripheral nervous system (PNS) and a central nervous system (CNS, comprising the brain and spinal cord), and is composed of two principal classes of cells: neurons and glial cells. The glial cells fill the spaces between neurons, nourishing them and modulating their function. Certain glial cells, such as Schwann cells in the PNS and oligodendrocytes in the CNS, also provide a protective myelin sheath that surrounds and protects neuronal axons, which are the processes that extend from the neuron cell body and through which the electric impulses of the neuron are transported. In the peripheral nervous system, the long axons of multiple neurons are bundled together to form a nerve or nerve fiber. These, in turn, may be combined into fascicles, wherein the nerve fibers form bundles embedded, together with the intraneural vascular supply, in a loose collagenous matrix bounded by a protective multilamellar sheath. In the central nervous system, the neuron cell bodies are visually distinguishable from their myelin-ensheathed processes, and are referenced in the art as gray and white matter, respectively.

During development, differentiating neurons from the central and peripheral nervous systems send out axons that must grow and make contact with specific target cells. In some cases, growing axons must cover enormous distances; some grow into the periphery, whereas others stay confined within the central nervous system. In mammals, this stage of neurogenesis is complete during the embryonic phase of life and neuronal cells do not multiply once they have fully differentiated.

Accordingly, the neural pathways of a mammal are particularly at risk if neurons are subjected to mechanical or chemical trauma or to neuropathic degeneration sufficient to put the neurons that define the pathway at risk of dying. A host of neuropathies, some of which affect only a subpopulation or a system of neurons in the peripheral or central nervous systems have been identified to date. The neuropathies, which may affect the neurons themselves or the associated glial cells, may result from cellular metabolic dysfunction, infection, exposure to toxic agents, autoimmunity dysfunction, malnutrition or ischemia. In some cases the cellular dysfunction is thought to induce cell death directly. In other cases, the neuropathy may induce sufficient tissue necrosis to stimulate the body's immune/inflammatory system and the mechanisms of the body's immune response to the initial neural injury then destroys the neurons and the pathway defined by these neurons.

Another common injury to the CNS is stroke, the destruction of brain tissue as a result of intracerebral hemorrhage or infarction. Stroke is a leading cause of death in the developed world. It may be caused by reduced blood flow or ischemia that results in deficient blood supply and death of tissues in one area of the brain (infarction). Causes of ischemic strokes include blood clots that form in the blood vessels in the brain (thrombus) and blood clots or pieces of atherosclerotic plaque or other material that travel to the brain from another location (emboli). Bleeding (hemorrhage) within the brain may also cause symptoms that mimic stroke. The ability to detect such injury is lacking in the prior art.

Mammalian neural pathways also are at risk due to damage caused by neoplastic lesions. Neoplasias of both the neurons and glial cells have been identified. Transformed cells of neural origin generally lose their ability to behave as normal differentiated cells and can destroy neural pathways by loss of function. In addition, the proliferating tumors may induce lesions by distorting normal nerve tissue structure, inhibiting pathways by compressing nerves, inhibiting cerebrospinal fluid or blood supply flow, and/or by stimulating the body's immune response. Metastatic tumors, which are a significant cause of neoplastic lesions in the brain and spinal cord, also similarly may damage neural pathways and induce neuronal cell death.

There is thus, a need in the art appropriate, specific, inexpensive and simple diagnostic clinical assessments of nervous system injury severity and therapeutic treatment efficacy. Thus identification of neurochemical markers that are specific to or predominantly found in the nervous system (CNS (brain and spinal cord) and PNS), would prove immensely beneficial for both prediction of outcome and for guidance of targeted therapeutic delivery.

SUMMARY

The present invention provides neuronal protein markers that are differentially present in the samples of patients suffering from neural injury and/or neuronal disorders as compared to samples of control subjects. The present invention also provides sensitive and quick methods and kits that can be used as an aid for diagnosis of neural injury and/or neuronal disorders by detecting these markers. The measurement of these markers, alone or in combination, in patient samples provides information that a diagnostician can correlate with a probable diagnosis of the extent of neural injury such as in traumatic brain injury (TBI) and stroke.

In a preferred embodiment, the invention provides biomarkers that are indicative of traumatic brain injury, neuronal damage, neural disorders, brain damage, neural damage due to drug or alcohol addiction, diseases associated with the brain or nervous system, such as the central nervous system. Preferably, the biomarkers are proteins, fragments or derivatives thereof, and are associated with neuronal cells, brain cells or any cell that is present in the brain and central nervous system.

In a preferred embodiment the biomarkers are preferably neural proteins, peptides, fragments or derivatives thereof. Examples of neural proteins, include, but are not limited to axonal proteins, amyloid precursor protein, dendritic proteins, somal proteins, presynaptic proteins, post-synaptic proteins and neural nuclear proteins.

In another preferred embodiment the biomarkers are selected from at least one protein, peptide, variant or fragment thereof, such as those proteins listed in Table 1 below. For example, Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GAB A-B-R2.

In another preferred embodiment the biomarkers are from at least two or more proteins, peptides, variants or fragments thereof, such as those proteins listed in Table 1 below. For example, Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GAB A-B-R2.

In another preferred embodiment, the biomarkers comprise at least one biomarker from each neural cell type. The composition of biomarkers is diagnostic of neural injury, damage and/or neural disorders. The composition comprises: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

In another preferred embodiment an expanded panel of biomarkers are used to provide highly enriched information of mechanism of injury, modes of cell death (necrosis versus apoptosis), sites of injury, sites and status of different cell types in the nervous system and enhanced diagnosis (better selectivity and specificity). This invention is an important and significant improvement over existing technologies focused on small panel (e.g. a four-marker panel: -MBP-Thrombomodulin-S100B-NSE from Syn X Pharma (Mississauga, Canada)- or single markers (e.g. S100B from DiaSorin (Sweden)).

In another preferred embodiment the biomarkers are selected to distinguish between different host anatomical regions. For example, at least one biomarker can be selected from neural subcellular protein biomarkers, nervous system anatomical markers such as hippocampus protein biomarkers and cerebellum protein biomarkers. Examples of neural subcellular protein biomarkers are NF-200, NF-160, NF-68. Examples of hippocampus protein biomarkers are SCG10, stathmin. An example of a cerebellum protein biomarker is Purkinje cell protein-2 (Pcp2).

In another preferred embodiment the biomarkers are selected to distinguish between injury at the cellular level, thereby detecting which cell type has been injured. For example at least one biomarker protein is selected from a representative panel of protein biomarkers specific for that cell type. Examples for biomarkers specific for cell types include myelin-oligodendrocyte biomarkers such as myelin basic protein (MBP), myelin proteolipid protein (PLP), myelin oligodendrocyte specific protein (MOSP), oligodendrocyte NS-1 protein, myelin oligodendrocyte glycoprotein (MOG). Examples of biomarkers specific for Schwann cells include, but not limited to Schwann cell myelin protein. Examples of Glial cell protein biomarkers include, but not limited to GFAP (protein accession number P47819), protein disulfide isomerase (PDI)-P04785. Thus, by detecting one or more specific biomarkers the specific cell types that have been injured can be determined.

In another preferred embodiment, biomarkers specific for different subcellular structures of a cell can be used to determine the subcellular level of injury. Examples include but not limited to neural subcellular protein biomarkers such as, NF-200, NF-160, NF-68; dendritic biomarkers such as for example, alpha-tubulin (P02551), beta-tubulin (P04691), MAP-2A/B, MAP-2C, Tau, Dynamin-1 (P212575), Phoecin, Dynactin (Q13561), p24 microtubule-associated protein, vimentin (P31000); somal proteins such as for example, UCH-L1 (Q00981), PEBP (P31044), NSE (P07323), CK-BB (P07335), Thy 1.1, prion protein, 14-3-3 proteins; neural nuclear proteins, such as for example S/G(2) nuclear autoantigen (SG2NA), NeuN. Thus, detection of specific biomarkers will determine the extent and subcellular location of injury.

In another preferred embodiment, biomarkers specific for different anatomical regions, different cell types, and/or different subcellular structures of a cell are selected to provide information as to the location of anatomical injury, the location of the injured cell type, and the location of injury at a subcellular level. Any number of biomarkers from each set can be used to provide highly enriched and detailed information of mechanism, mode and subcellular sites of injury, anatomical locations of injury and status of different cell types in the nervous system (neuronal subtypes, neural stem cells, astro-glia, oligodendrocyte and microglia cell).

In a preferred embodiment at least one biomarker specific different locations such as for an anatomical region, different cell types and/or different subcellular structures of a cell are used to determine the mechanism, mode, subcellular sites of injury, anatomical locations of injury and status of different cell types in the nervous system, more preferably a panel of at least 2 biomarkers are selected from each desired location, more preferably at least 3, 4, 5, 6, 7, 8, 9, 10 up to about 100 biomarkers are selected from each location.

In a preferred embodiment, subcellular neuronal biomarkers for diagnosis and detection of brain and/or CNS injury and/or neural disorders, preferably are at least one of axonal proteins, dendritic proteins, somal proteins, neural nuclear proteins, presynaptic proteins, post-synaptic proteins.

In a preferred embodiment, axonal proteins identified as biomarkers for diagnosis and detection of brain and/or CNS injury or neural disorders, preferably are: α II spectrin (and SPDB)-1, NF-68 (NF-L)-2, Tau-3, α II, III spectrin, NF-200 (NF-H), NF-160 (NF-M), Amyloid precursor protein, α internexin, peptides, fragments or derivatives thereof.

In a preferred embodiment, dendritic proteins identified as biomarkers for diagnosis and detection of brain and/or CNS injury or neural disorders, preferably are: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2, peptides, fragments or derivatives thereof.

In another preferred embodiment, neural nuclear proteins identified as biomarkers for diagnosis and detection of brain and/or CNS injury or neural disorders, preferably are: NeuN-1, S/G(2) nuclear autoantigen (SG2NA), Huntingtin, peptides or fragments thereof.

In another preferred embodiment, somal proteins identified as biomarkers for diagnosis and detection of brain and/or CNS injury or neural disorders, preferably are: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22, peptides, fragments or derivatives thereof.

In another preferred embodiment, presynaptic proteins identified as biomarkers for diagnosis and detection of brain and/or CNS injury or neural disorders, preferably are: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477), peptides, fragments or derivatives thereof.

In another preferred embodiment, post-synaptic proteins identified as biomarkers for diagnosis and detection of brain and/or CNS injury or neural disorders, preferably are: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP, peptides, fragments or derivatives thereof.

In another preferred embodiment, identified biomarkers distinguish the damaged neural cell subtype such as, for example, myelin-oligodendrocytes, glial, microglial, Schwann cells, glial scar.

In a preferred embodiment, Myelin-Oligodendrocyte biomarkers are: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)—P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin.

In another preferred embodiment, biomarkers identifying the anatomical location of neural injury and/or neural damage, include, but not limited to: Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); PH8 (S Serotonergic Dopaminergic), PEP-19, Neurocalcin (NC), a neuron-specific EF-hand $Ca^{2+}$-binding protein, Encephalopsin, Striatin, SG2NA, Zinedin, Recoverin, and Visinin.

In another preferred embodiment, biomarkers identifying damaged neural subtypes include, but not limited to: Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GABA-B-R2.

Demyelination proteins identified as biomarkers for diagnosis and detection of brain and/or CNS injury or neural disorders, preferably are: myelin basic protein (MBP), myelin proteolipid protein, peptides, fragments or derivatives thereof.

In another preferred embodiment, glial proteins identified as biomarkers for diagnosis and detection of brain and/or CNS injury or neural disorders, preferably are: GFAP (P47819), protein disulfide isomerase (PDI—P04785), peptides, fragments and derivatives thereof.

In another preferred embodiment, cholinergic proteins identified as biomarkers for diagnosis and detection of brain and/or CNS injury or neural disorders, preferably are: acetylcholine esterase, choline acetyltransferase, peptides, fragments or derivatives thereof.

In another preferred embodiment, dopaminergic proteins identified as biomarkers for diagnosis and detection of brain and/or CNS injury or neural disorders, preferably are: tyrosine hydroxylase (TH), phospho-TH, DARPP32, peptides, fragments or derivatives thereof.

In another preferred embodiment, noradrenergic proteins identified as biomarkers for diagnosis and detection of brain and/or CNS injury or neural disorders, preferably are: dopamine beta-hydroxylase (DbH), peptides, fragments or derivatives thereof.

In another preferred embodiment, serotonergic proteins identified as biomarkers for diagnosis and detection of brain and/or CNS injury or neural disorders, preferably are: tryptophan hydroxylase (TrH), peptides, fragments or derivatives thereof.

In another preferred embodiment, glutamatergic proteins identified as biomarkers for diagnosis and detection of brain and/or CNS injury or neural disorders, preferably are: glutaminase, glutamine synthetase, peptides, fragments or derivatives thereof.

In another preferred embodiment, GABAergic proteins identified as biomarkers for diagnosis and detection of brain and/or CNS injury or neural disorders, preferably are: GABA transaminase (4-aminobutyrate-2-ketoglutarate transaminase [GABAT]), glutamic acid decarboxylase (GAD25, 44, 65, 67), peptides, fragments and derivatives thereof.

In another preferred embodiment, neurotransmitter receptors identified as biomarkers for diagnosis and detection of brain and/or CNS injury or neural disorders, preferably are: beta-adrenoreceptor subtypes, (e.g. beta (2)), alpha-adrenoreceptor subtypes, (e.g. (alpha (2c)), GABA receptors (e.g. GABA(B)), metabotropic glutamate receptor (e.g. mGluR3), NMDA receptor subunits (e.g. NR1A2B), Glutamate receptor subunits (e.g. GluR4), 5-HT serotonin receptors (e.g. 5-HT(3)), dopamine receptors (e.g. D4), muscarinic Ach receptors (e.g. M1), nicotinic acetylcholine receptor (e.g. alpha-7), peptides, fragments or derivatives thereof.

In another preferred embodiment, neurotransmitter transporters identified as biomarkers for diagnosis and detection of brain and/or CNS injury or neural disorders, preferably are: norepinephrine transporter (NET), dopamine transporter (DAT), serotonin transporter (SERT), vesicular transporter proteins (VMAT1 and VMAT2), GABA transporter vesicular inhibitory amino acid transporter (VIAAT/VGAT), glutamate transporter (e.g. GLT1), vesicular acetylcholine transporter, choline transporter (e.g. CHT1), peptides, fragments, or derivatives thereof.

In another preferred embodiment, other proteins identified as biomarkers for diagnosis and detection of brain and/or CNS injury or neural disorders, include, but are not limited to vimentin (P31000), CK-BB (P07335), 14-3-3-epsilon (P42655), MMP2, MMP9, peptides, fragments or derivatives thereof.

The markers are characterized by molecular weight, enzyme digested fingerprints and by their known protein identities. The markers can be resolved from other proteins in a sample by using a variety of fractionation techniques, e.g., chromatographic separation coupled with mass spectrometry, or by traditional immunoassays. In preferred embodiments, the method of resolution involves Surface-Enhanced Laser Desorption/Ionization ("SELDI") mass spectrometry, in which the surface of the mass spectrometry probe comprises adsorbents that bind the markers.

In other preferred embodiments, a plurality of the biomarkers are detected, preferably at least two of the biomarkers are detected, more preferably at least three of the biomarkers are detected, most preferably at least four of the biomarkers are detected.

In one aspect, the amount of each biomarker is measured in the subject sample and the ratio of the amounts between the markers is determined. Preferably, the amount of each biomarker in the subject sample and the ratio of the amounts between the biomarkers and compared to normal healthy individuals. The increase in ratio of amounts of biomarkers between healthy individuals and individuals suffering from injury is indicative of the injury magnitude, disorder progression as compared to clinically relevant data.

Preferably, biomarkers that are detected at different stages of injury and clinical disease are correlated to assess anatomical injury, type of cellular injury, subcellular localization of injury. Monitoring of which biomarkers are detected at which stage, degree of injury in disease or physical injury will provide panels of biomarkers that provide specific information on mechanisms of injury, identify multiple subcellular sites of injury, identify multiple cell types involved in disease related injury and identify the anatomical location of injury.

In another aspect, preferably a single biomarker is used in combination with one or more biomarkers from normal, healthy individuals for diagnosing injury, location of injury and progression of disease and/or neural injury, more preferably a plurality of the markers are used in combination with one or more biomarkers from normal, healthy individuals for diagnosing injury, location of injury and progression of disease and/or neural injury. It is preferred that one or more protein biomarkers are used in comparing protein profiles from patients susceptible to, or suffering from disease and/or neural injury, with normal subjects.

Preferred detection methods include use of a biochip array. Biochip arrays useful in the invention include protein and nucleic acid arrays. One or more markers are immobilized on the biochip array and subjected to laser ionization to detect the molecular weight of the markers. Analysis of the markers is, for example, by molecular weight of the one or more markers against a threshold intensity that is normalized against total ion current. Preferably, logarithmic transformation is used for reducing peak intensity ranges to limit the number of markers detected.

In another preferred method, data is generated on immobilized subject samples on a biochip array, by subjecting said biochip array to laser ionization and detecting intensity of signal for mass/charge ratio; and, transforming the data into computer readable form; and executing an algorithm that classifies the data according to user input parameters, for detecting signals that represent markers present in injured and/or diseased patients and are lacking in non-injured and/or diseased subject controls.

Preferably the biochip surfaces are, for example, ionic, anionic, comprised of immobilized nickel ions. comprised of a mixture of positive and negative ions, comprises one or more antibodies, single or double stranded nucleic acids, comprises proteins, peptides or fragments thereof, amino acid probes, comprises phage display libraries.

In other preferred methods one or more of the markers are detected using laser desorption/ionization mass spectrometry, comprising, providing a probe adapted for use with a mass spectrometer comprising an adsorbent attached thereto, and; contacting the subject sample with the adsorbent, and; desorbing and ionizing the marker or markers from the probe and detecting the deionized/ionized markers with the mass spectrometer.

Preferably, the laser desorption/ionization mass spectrometry comprises, providing a substrate comprising an adsorbent attached thereto; contacting the subject sample with the adsorbent; placing the substrate on a probe adapted for use with a mass spectrometer comprising an adsorbent attached thereto; and, desorbing and ionizing the marker or markers from the probe and detecting the desorbed/ionized marker or markers with the mass spectrometer.

The adsorbent can for example be, hydrophobic, hydrophilic, ionic or metal chelate adsorbent, such as, nickel or an antibody, single- or double stranded oligonucleotide, amino acid, protein, peptide or fragments thereof.

In another embodiment, a process for purification of a biomarker, comprising fractioning a sample comprising one or more protein biomarkers by size-exclusion chromatography and collecting a fraction that includes the one or more biomarker; and/or fractionating a sample comprising the one or more biomarkers by anion exchange chromatography and collecting a fraction that includes the one or more biomarkers. Fractionation is monitored for purity on normal phase and immobilized nickel arrays. Generating data on immobilized marker fractions on an array, is accomplished by subjecting said array to laser ionization and detecting intensity of signal for mass/charge ratio; and, transforming the data into computer readable form; and executing an algorithm that classifies the data according to user input parameters, for detecting signals that represent markers present in injured and/or diseased patients and are lacking in non-injured and/or diseased subject controls. Preferably fractions are subjected to gel electrophoresis and correlated with data generated by mass spectrometry. In one aspect, gel bands representative of potential markers are excised and subjected to enzymatic treatment and are applied to biochip arrays for peptide mapping.

In another preferred embodiment, the presence of certain biomarkers is indicative of the extent of CNS and/or brain injury. For example, detection of one or more dendritic damage markers, soma injury markers, demyelination markers, axonal injury markers would be indicative of CNS injury and the presence of one or more would be indicative of the extent of nerve injury.

In another preferred embodiment, the presence of certain biomarkers is indicative of a neurological disorder. i.e. dendritic damage markers, soma injury markers, demyelination markers, axonal injury markers, synaptic terminal markers, post-synaptic markers.

Preferred methods for detection and diagnosis of CNS/PNS and/or brain injury comprise detecting at least one or more protein biomarkers in a subject sample, and; correlating the detection of one or more protein biomarkers with a diagnosis of CNS and/or brain injury, wherein the correlation takes into account the detection of one or more biomarker in each diagnosis, as compared to normal subjects, wherein the one or more protein markers are selected from: neural proteins, such as for example, Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G (2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon(NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha(2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GABA-B-R2.

In another preferred embodiment, the invention provides a kit for analyzing cell damage in a subject. The kit, preferably includes: (a) one or more biomarkers (b) a substrate for holding a biological sample isolated from a human subject suspected of having a damaged nerve cell, (c) an agent that specifically binds at least one or more of the neural proteins; and (d) printed instructions for reacting the agent with the biological sample or a portion of the biological sample to detect the presence or amount of at least one marker in the biological sample. The biomarkers include but not limited to: Axonal Proteins: α II spectrin (and SPDB)-1, NF-68 (NF-L)-2, Tau-3, α II, III spectrin, NF-200 (NF-H), NF-160 (NF-M), Amyloid precursor protein, a internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GABA-B-R2.

In another preferred embodiment, the kit comprises a composition or panel of biomarkers comprises: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

Preferably, the biological sample is a fluid in communication with the nervous system of the subject prior to being isolated from the subject; for example, CSF or blood, and the agent can be an antibody, aptamer, or other molecule that specifically binds at least one or more of the neural proteins. The kit can also include a detectable label such as one conjugated to the agent, or one conjugated to a substance that specifically binds to the agent (e.g., a secondary antibody).

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
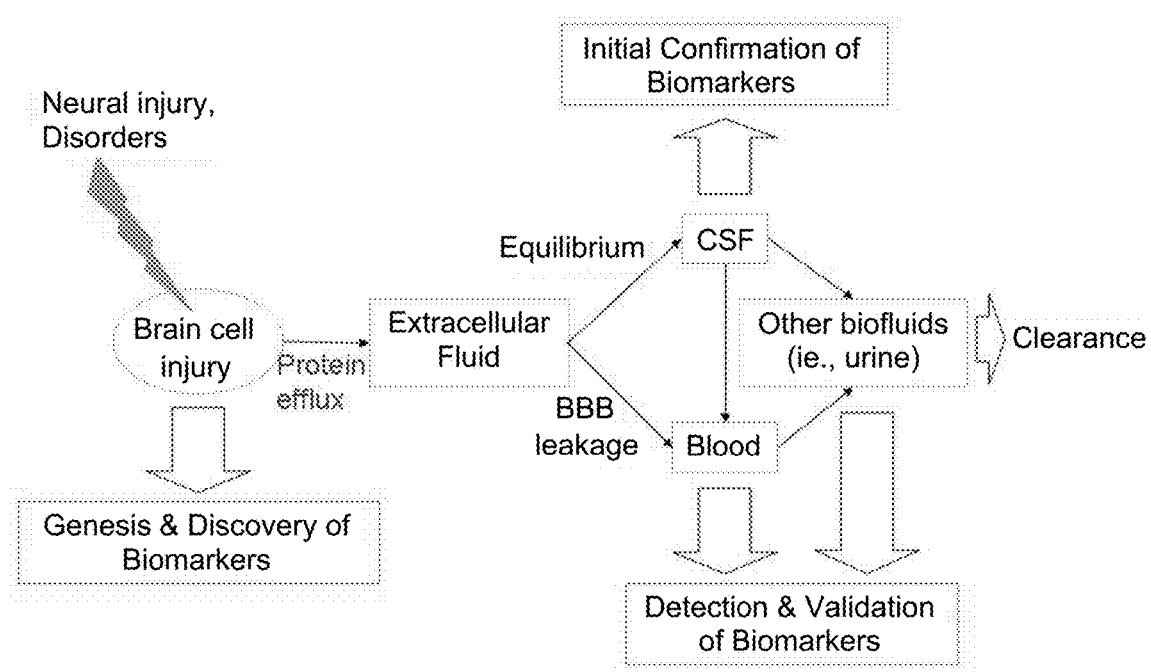
FIG. 1 is a schematic illustration showing the fate of brain injury biomarkers. The pathway of genesis of biomarkers from the brain to the eventual release of such biomarkers into biofluids, such as CSF, blood, urine, saliva, sweat etc. provide a opportunity for biomarker detection with low invasiveness.

The present invention identifies biomarkers that are diagnostic of nerve cell injury and/or neuronal disorders. Detection of different biomarkers of the invention are also diagnostic of the degree of severity of nerve injury, the cell(s) involved in the injury, and the subcellular localization of the injury. In particular, the invention employs a step of correlating the presence or amount of one or more neural protein(s) with the severity and/or type of nerve cell injury. The amount of a neural protein, fragment or derivative thereof directly relates to severity of nerve tissue injury as a more severe injury damages a greater number of nerve cells which in turn causes a larger amount of neural protein(s) to accumulate in the biological sample (e.g., CSF).

Prior to setting forth the invention, it may be helpful to an understanding thereof to set forth definitions of certain terms that will be used hereinafter.

"Marker" in the context of the present invention refers to a polypeptide (of a particular apparent molecular weight) which is differentially present in a sample taken from patients having neural injury and/or neuronal disorders as compared to a comparable sample taken from control subjects (e.g., a person with a negative diagnosis, normal or healthy subject).

"Complementary" in the context of the present invention refers to detection of at least two biomarkers, which when detected together provides increased sensitivity and specificity as compared to detection of one biomarker alone.

The phrase "differentially present" refers to differences in the quantity and/or the frequency of a marker present in a sample taken from patients having for example, neural injury as compared to a control subject. For example, a marker can be a polypeptide which is present at an elevated level or at a decreased level in samples of patients with neural injury compared to samples of control subjects. Alternatively, a marker can be a polypeptide which is detected at a higher frequency or at a lower frequency in samples of patients compared to samples of control subjects. A marker can be differentially present in terms of quantity, frequency or both.

A polypeptide is differentially present between the two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between the two sets of samples if the frequency of detecting the polypeptide in samples of patients' suffering from neural injury and/or neuronal disorders, is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of neural injury and/or neuronal disorder. A diagnostic amount can be either in absolute amount (e.g., µg/ml) or a relative amount (e.g., relative intensity of signals).

A "control amount" of a marker can be any amount or a range of amount which is to be compared against a test amount of a marker. For example, a control amount of a marker can be the amount of a marker in a person without neural injury and/or neuronal disorder. A control amount can be either in absolute amount (e.g., µg/ml) or a relative amount (e.g., relative intensity of signals).

"Probe" refers to a device that is removably insertable into a gas phase ion spectrometer and comprises a substrate having a surface for presenting a marker for detection. A probe can comprise a single substrate or a plurality of substrates.

"Substrate" or "probe substrate" refers to a solid phase onto which an adsorbent can be provided (e.g., by attachment, deposition, etc.).

"Adsorbent" refers to any material capable of adsorbing a marker. The term "adsorbent" is used herein to refer both to a single material ("monoplex adsorbent") (e.g., a compound or functional group) to which the marker is exposed, and to a plurality of different materials ("multiplex adsorbent") to which the marker is exposed. The adsorbent materials in a multiplex adsorbent are referred to as "adsorbent species." For example, an addressable location on a probe substrate can comprise a multiplex adsorbent characterized by many different adsorbent species (e.g., anion exchange materials, metal chelators, or antibodies), having different binding characteristics. Substrate material itself can also contribute to adsorbing a marker and may be considered part of an "adsorbent."

"Adsorption" or "retention" refers to the detectable binding between an absorbent and a marker either before or after washing with an eluant (selectivity threshold modifier) or a washing solution.

"Eluant" or "washing solution" refers to an agent that can be used to mediate adsorption of a marker to an adsorbent. Eluants and washing solutions are also referred to as "selectivity threshold modifiers." Eluants and washing solutions can be used to wash and remove unbound materials from the probe substrate surface.

"Resolve," "resolution," or "resolution of marker" refers to the detection of at least one marker in a sample. Resolution includes the detection of a plurality of markers in a sample by separation and subsequent differential detection. Resolution does not require the complete separation of one or more markers from all other biomolecules in a mixture. Rather, any separation that allows the distinction between at least one marker and other biomolecules suffices.

"Gas phase ion spectrometer" refers to an apparatus that measures a parameter which can be translated into mass-to-charge ratios of ions formed when a sample is volatilized and ionized. Generally ions of interest bear a single charge, and mass-to-charge ratios are often simply referred to as mass. Gas phase ion spectrometers include, for example, mass spectrometers, ion mobility spectrometers, and total ion current measuring devices.

"Mass spectrometer" refers to a gas phase ion spectrometer that includes an inlet system, an ionization source, an ion optic assembly, a mass analyzer, and a detector.

"Laser desorption mass spectrometer" refers to a mass spectrometer which uses laser as means to desorb, volatilize, and ionize an analyte.

"Detect" refers to identifying the presence, absence or amount of the object to be detected.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker NF-200 from specific species such as rat, mouse, or human can be selected to obtain only those polyclonal antibodies that are specifically immunoreactive with marker NF-200 and not with other proteins, except for polymorphic variants and alleles of marker NF-200. This selection may be achieved by subtracting out antibodies that cross-react with marker NF-200 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Energy absorbing molecule" or "EAM" refers to a molecule that absorbs energy from an ionization source in a mass spectrometer thereby aiding desorption of analyte, such as a marker, from a probe surface. Depending on the size and nature of the analyte, the energy absorbing molecule can be optionally used. Energy absorbing molecules used in MALDI are frequently referred to as "matrix." Cinnamic acid derivatives, sinapinic acid ("SPA"), cyano hydroxy cinnamic acid ("CHCA") and dihydroxybenzoic acid are frequently used as energy absorbing molecules in laser desorption of bioorganic molecules.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

As used herein, the term "injury or neural injury" is intended to include a damage which directly or indirectly affects the normal functioning of the CNS. For example, the injury can be damage to retinal ganglion cells; a traumatic brain injury; a stroke related injury; a cerebral aneurism related injury; a spinal cord injury, including monoplegia, diplegia, paraplegia, hemiplegia and quadriplegia; a neuroproliferative disorder or neuropathic pain syndrome. Examples of CNS injuries or disease include TBI, stroke, concussion (including post-concussion syndrome), cerebral ischemia, neurodegenerative diseases of the brain such as Parkinson's disease, Dementia Pugilistica, Huntington's disease and Alzheimer's disease, Creutzfeldt-Jakob disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, trypanosomes, malarial pathogens, and other CNS traumas.

As used herein, the term "stroke" is art recognized and is intended to include sudden diminution or loss of consciousness, sensation, and voluntary motion caused by rapture or obstruction (e.g. by a blood clot) of an artery of the brain.

As used herein, the term "Traumatic Brain Injury" is art recognized and is intended to include the condition in which, a traumatic blow to the head causes damage to the brain, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF).

"Neural cells" as defined herein, are cells that reside in the brain, central and peripheral nerve systems, including, but not limited to, nerve cells, glial cell, oligodendrocyte, microglia cells or neural stem cells.

"Neuronal specific or neuronally enriched proteins" are defined herein, as proteins that are present in neural cells and not in non-neuronal cells, such as, for example, cardiomyocytes, myocytes, in skeletal muscles, hepatocytes, kidney cells and cells in testis. Non-limiting examples of neural proteins are shown in Table 1 below.

"Neural (neuronal) defects, disorders or diseases" as used herein refers to any neurological disorder, including but not limited to neurodegenerative disorders (Parkinson's; Alzheimer's) or autoimmune disorders (multiple sclerosis) of the central nervous system; memory loss; long term and short term memory disorders; learning disorders; autism, depression, benign forgetfulness, childhood learning disorders, close head injury, and attention deficit disorder; autoimmune disorders of the brain, neuronal reaction to viral infection; brain damage; depression; psychiatric disorders such as bi-polarism, schizophrenia and the like; narcolepsy/sleep disorders(including circadian rhythm disorders, insomnia and narcolepsy); severance of nerves or nerve damage; severance of the cerebrospinal nerve cord (CNS) and any damage to brain or nerve cells; neurological deficits associated with AIDS; tics (e.g. Giles de la Tourette's syndrome); Huntington's chorea, schizophrenia, traumatic brain injury, tinnitus, neuralgia, especially trigeminal neuralgia, neuropathic pain, inappropriate neuronal activity resulting in neurodysthesias in diseases such as diabetes, MS and motor neurone disease, ataxias, muscular rigidity (spasticity) and temporomandibular joint dysfunction; Reward Deficiency Syndrome (RDS) behaviors in a subject.

As used herein, "RDS" behaviors are those behaviors that manifests as one or more behavioral disorders related to an individual's feeling of well-being with anxiety, anger or a craving for a substance. RDS behaviors include, alcoholism, SUD, smoking, BMI or obesity, pathological gambling, carbohydrate bingeing, axis 11 diagnosis, SAB, ADD/ADHD, CD, TS, family history of SUD, and Obesity. All these behaviors, and others described herein as associated with RDS behaviors or genes involved in the neurological pathways related to RDS, are included as RDS behaviors as part of this invention. Additionally, many of the clinical terms used herein for many specific disorders that are RDS disorders are found in the Quick Reference to the Diagnostic Criteria From DSM-IV™, The American Psychiatric Association, Washington, D.C., 1994.

Affective disorders, including major depression, and the bipolar, manic-depressive illness, are characterized by changes in mood as the primary clinical manifestation. Major depression is the most common of the significant mental illnesses, and it must be distinguished clinically from periods of normal grief, sadness and disappointment, and the related dysphoria or demoralization frequently associated with medical illness. Depression is characterized by feelings of intense sadness, and despair, mental slowing and loss of concentration, pessimistic worry, agitation, and self-deprecation. Physical changes can also occur, including insomnia, anorexia, and weight loss, decreased energy and libido, and disruption of hormonal circadian rhythms.

Mania, as well as depression, is characterized by changes in mood as the primary symptom. Either of these two extremes of mood may be accompanied by psychosis with disordered thought and delusional perceptions. Psychosis may have, as a secondary symptom, a change in mood, and it is this overlap with depression that causes much confusion in diagnosis. Severe mood changes without psychosis frequently occur in depression and are often accompanied by anxiety.

Parkinson's disease, independent of a specific etiology, is a chronic, progressive central nervous system disorder which usually appears insidiously in the latter decades of life. The disease produces a slowly increasing disability in purposeful movement. It is characterized by four major clinical features of tremor, bradykinesia, rigidity and a disturbance of posture. Often patients have an accompanying dementia. In idiopathic Parkinsonism, there is usually a loss of cells in the substantia nigra, locus ceruleus, and other pigmented neurons of the brain, and a decrease of dopamine content in nerve axon terminals of cells projecting from the substantia nigra. The understanding that Parkinsonism is a syndrome of dopamine deficiency and the discovery of levodopa as an important drug for the treatment of the disease were the logical culmination of a series of related basic and clinical observations, which serves as the rationale for drug treatment.

As used herein, the term "schizophrenia" refers to a psychiatric disorder that includes at least two of the following: delusions, hallucinations, disorganized speech, grossly disorganized or catatonic behavior, or negative symptoms. (APA, 1994, Diagnostic and Statistical Manual of Mental Disorders (Fourth Edition), Washington, D.C.).

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann et al., 1984, Neurology 34:939-944). The patient's cognitive function can be assessed by the Alzheimer's Disease Assessment Scale-cognitive subscale (ADAS-cog; Rosen et al., 1984, Am. J. Psychiatry 141:1356-1364).

As used herein, the term "autism" refers to a state of mental introversion characterized by morbid self-absorption, social failure, language delay, and stereotyped behavior.

As used herein, the term "depression" refers to a clinical syndrome that includes a persistent sad mood or loss of interest in activities, which lasts for at least two weeks in the absence of treatment.

The term "benign forgetfulness," as used herein, refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale (Russell, 1975, *J. Consult Clin. Psychol.* 43:800-809).

As used herein, the term "childhood learning disorders" refers to an impaired ability to learn, as experienced by certain children.

The term "close head injury," as used herein, refers to a clinical condition after head injury or trauma which condition can be characterized by cognitive and memory impairment. Such a condition can be diagnosed as "amnestic disorder due to a general medical condition" according to DSM-IV.

The term "attention deficit disorder," as used herein, refers to a disorder that is most commonly exhibited by children and which can be characterized by increased motor activity and a decreased attention span. Attention-deficit disorder ("ADD") is a common behavioral learning disorder in children which adversely affects school performance and family relationships. Symptoms and signs include hyperactivity (e.g., ADDH and AD/HD, DSM-IV), impulsivity, emotional lability, motor incoordination and some perceptual difficulties. Treatment has included psychostimulants, which while effective are controversial, and may cause troubling side effects such as dysphoria, headache and growth retardation. Other drugs, including the tricyclic antidepressants, appear to improve attention, but may be less effective than the psychostimulants.

Figure 2:
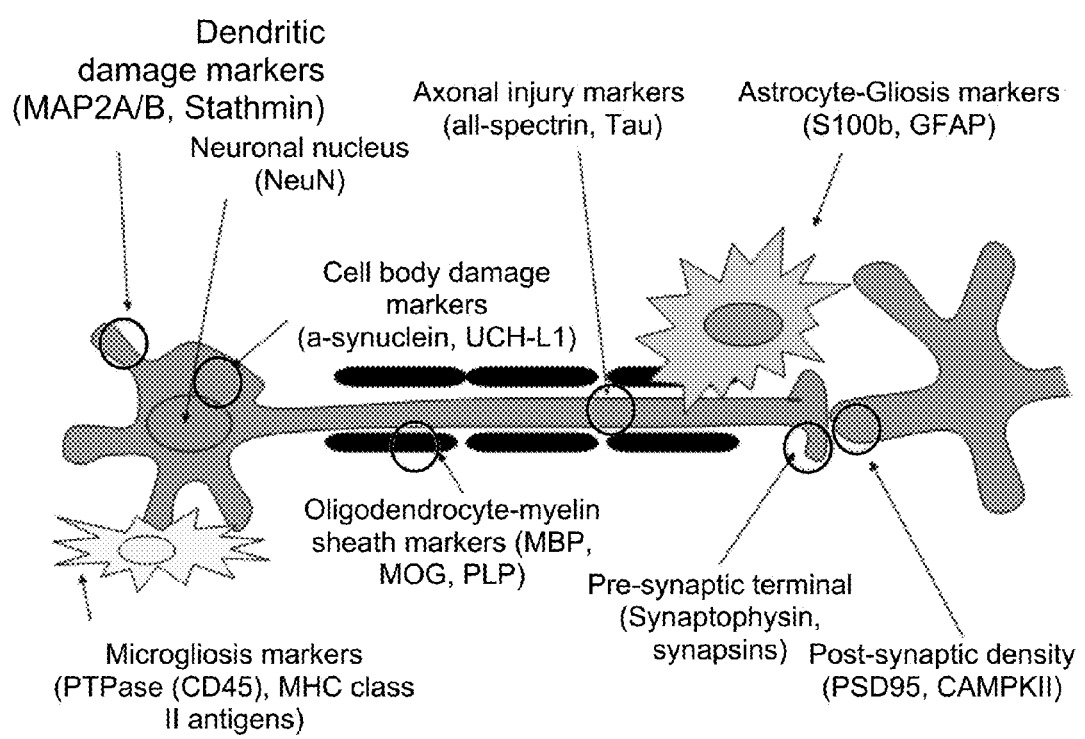
FIG. 2 is a schematic illustration showing sources of brain injury biomarkers from different cell types (neurons, astroglia cells, Microglia cells, oligodendrocyte or Schwann cell) and from different subcellular structural structure of a neuron (dendrites, axons, cell body, presynaptic terminal and postsynaptic density)

As used herein, "subcellular localization" refers to defined subcellular structures within a single nerve cell. These subcellularly defined structures are matched with unique neural proteins derived from, for example, dendritic, axonal, myelin sheath, presynaptic terminal and postsynaptic locations as illustrated in FIG. 2. By monitoring the release of proteins unique to each of these regions, one can therefore monitor and define subcellular damage after brain injury. Furthermore, mature neurons are differentiated into dedicated subtype fusing a primary neural transmitter such as cholinergic (nicotinic and mucarinic), glutamatergic, gabaergic, serotonergic, dopaminergic. Each of this neuronal subtype express unique neural proteins such as those dedicated for the synthesis, metabolism and transporter and receptor of each unique neurotransmitter system (Table 1).

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "patient" or "individual" are used interchangeably herein, and is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, "ameliorated" or "treatment" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests. For example, amelioration or treatment of depression includes, for example, relief from the symptoms of depression which include, but are not limited to changes in mood, feelings of intense sadness and despair, mental slowing, loss of concentration, pessimistic worry, agitation, and self-deprecation. Physical changes may also be relieved, including insomnia, anorexia and weight loss, decreased energy and libido, and the return of normal hormonal circadian rhythms. Another example, when using the terms "treating Parkinson's disease" or "ameliorating" as used herein means relief from the symptoms of Parkinson's disease which include, but are not limited to tremor, bradykinesia, rigidity, and a disturbance of posture.

Protein Biomarkers

In a preferred embodiment, detection of one or more neural biomarkers is diagnostic of neural damage and/or neuronal disease. Examples of neural biomarkers, include but are not limited to: neural proteins, such as for example, axonal proteins—NF-200 (NF-H), NF-160 (NF-M), NF-68 (NF-L); amyloid precursor protein; dendritic proteins—alpha-tubulin (P02551), beta-tubulin (P0 4691), MAP-2A/B, MAP-2C, Tau, Dynamin-1 (P21575), Dynactin (Q13561), P24; somal proteins—UCH-L1 (Q00981), PEBP (P31044), NSE (P07323), Thy 1.1, Prion, Huntington; pre-synaptic proteins—synapsin-1, synapsin-2, alpha-synuclein (p3'73'7'7), beta-synuclein (Q63754), GAP43, synaptophysin, synaptotagmin (P21707), syntaxin; post-synaptic proteins—PSD95, PSD93, NMDA-receptor (including all subtypes); demyelination biomarkers-myelin basic protein (MBP), myelin proteolipid protein; glial proteins—GFAP (P47819), protein disulfide isomerase (PDI-P04785); neurotransmitter biomarkers-cholinergic biomarkers: acetylcholine esterase, choline acetyltransferase; dopaminergic biomarkers-tyrosine hydroxylase (TH), phospho-TH, DARPP32; noradrenergic biomarkers-dopamine beta-hydroxylase (DbH); serotonergic biomarkers-tryptophan hydroxylase (TrH); glutamatergic biomarkers-glutaminase, glutamine synthetase; GABAergic biomarkers-GABA transaminase (4-aminobutyrate-2-ketoglutarate transaminase [GABAT]), glutamic acid decarboxylase (GAD25, 44, 65, 67); neurotransmitter receptors-beta-adrenoreceptor subtypes, (e.g. beta (2)), alpha-adrenoreceptor subtypes, (e.g. (alpha (2c)), GABA receptors (e.g. GABA(B)), metabotropic glutamate receptor (e.g. mGluR3), NMDA receptor subunits (e.g. NR1A2B), Glutamate receptor subunits (e.g. GluR4), 5-HT serotonin receptors (e.g. 5-HT(3)), dopamine receptors (e.g. D4), muscarinic Ach receptors (e.g. M1), nicotinic acetylcholine receptor (e.g. alpha-7); neurotransmitter transporters-norepinephrine transporter (NET), dopamine transporter (DAT), serotonin transporter (SERT), vesicular transporter proteins (VMAT1 and VMAT2), GABA transporter vesicular inhibitory amino acid transporter (VIAAT/VGAT), glutamate transporter (e.g. GLT1), vesicular acetylcholine transporter, choline transporter (e.g. CHT1); other protein biomarkers include, but not limited to vimentin (P31000), CK-BB (P07335), 14-3-3-epsilon (P42655), MMP2, MMP9.

In another preferred embodiment, a composition or panel of biomarkers comprises: Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2

(NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GAB A-B-R2.

In another preferred embodiment, the panel of biomarkers comprise at least one biomarker from each neural cell type. The composition of biomarkers is diagnostic of neural injury, damage and/or neural disorders. The composition comprises: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

Without wishing to be bound by theory, upon injury, structural and functional integrity of the cell membrane and blood brain barrier are compromised. Brain-specific and brain-enriched proteins are released into the extracellular space and subsequently into the CSF and blood. This is shown in a schematic illustration in FIG. 1.

In a preferred embodiment, detection of at least one neural protein in CSF, blood, or other biological fluids, is diagnostic of the severity of brain injury and/or the monitoring of the progression of therapy. Preferably, the neural proteins are detected during the early stages of injury. An increase in the amount of neural proteins, fragments or derivatives thereof, in a patient suffering from a neural injury, neuronal disorder as compared to a normal healthy individual, will be diagnostic of a neural injury and/or neuronal disorder.

In another preferred embodiment, detection of at least one neural protein in CSF, blood, or other biological fluids, is diagnostic of the severity of injury following a variety of CNS insults, such as for example, stroke, spinal cord injury, or neurotoxicity caused by alcohol or substance abuse (e.g. ecstacy, methamphetamine, etc.)

In a preferred embodiment, biomarkers of brain injury, neural injury and/or neural disorders comprises proteins from the neural system (CNS and PNS). The CNS comprises many brain-specific and brain-enriched proteins that are preferable biomarkers in the diagnosis of brain injury, neural injury, neural disorders and the like. Non-limiting examples are shown in Table 1 and FIG. 2. For example, the neural specific biomarkers can include Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin 1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GABA-B-R2. Furthermore, proteins such as GFAP and protein disulfide isomerase (PDI) are only synthesized in glial cells of the CNS, a feature that is used to further detect and diagnose the extent of damage to the CNS.

In another preferred embodiment, the invention provides for the quantitative detection of damage to the CNS, PNS and/or brain injury at a subcellular level. Depending on the type and severity of injury, neurons can undergo damage in specific cellular regions. For example, detection of certain biomarkers, such as for example, axonal proteins, fragments and derivatives thereof include, but not limited to: NF-200 (NF-H), NF-160 (NF-M), NF-68 (NF-L), and the like, differentiates between axonal versus dendritic damage. Non-limiting examples of dendritic proteins, peptides, fragments and derivatives thereof, include, but not limited to: alpha-tubulin (P02551), beta-tubulin (P0 4691), MAP-2A/B, MAP-2C, Tau, Dynamin-1 (P21575), Dynactin (Q13561), p24 (neural-specific MAP). Furthermore, detection of different biomarkers not only differentiate between, for example, axonal or dendritic damage, but allow for the assessment of synaptic pathology, specific injury to elements of the pre-synaptic terminal and post-synaptic density. See table 1 for examples of biomarkers from each cellular, sub-cellular and anatomical locations, detection of which detects the location of injury.

In a preferred embodiment, biomarkers indicative of neural injury in different anatomical in vivo locations include but not limited to: Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin. For example, to determine injury in a certain anatomical location, detection of Stathmin and/or Hippocalcin and/or SCG10 is diagnostic of injury in the Hippocampus. Detection of Purkinje cell protein-2 (Pcp2) and/or Calbindin D9K and/or Calbindin D28K (NP_114190) and/or Cerebellar CaBP, spot 35 is diagnostic of injury in the cerebellum. Detection of a combination of biomarkers, such as Stathmin and/or Hippocalcin and/or SCG10 Purkinje cell protein-2 (Pcp2) and/or Calbindin D9K and/or Calbindin D28K (NP_114190) and/or Cerebellar CaBP, spot 35 is diagnostic of injury in the Hippocampus and cerebellum. Therefore, detection of one or more or combinations of biomarkers is diagnostic of the location of neural injury.

In another preferred embodiment, the amount of marker detected, for example, in µg/ml is diagnostic of the extent of damage or injury. Quantitation of each biomarker is described in the specification and in the Examples to follow. Assays include immunoassays (such as ELISA's), spectrophotometry, HPLC, SELDI, biochips and the like. Therefore, if for example, 10 µg/ml of stathmin and 0.001 µg/ml of CaBP is diagnostic that the main injury is to the Hippocampus with some injury to the cerebellum. Detection of biomarkers from subcellular locations is diagnostic of which cells are injured. For example, detection of axonal biomarkers vs. dendritic biomarkers vs. microglial biomarkers is diagnostic of the type of cells injured. As discussed, infra, the quantitation of each as compared to a normal individual is diagnostic of the extent of injury.

In another preferred embodiment, detection of certain biomarkers are diagnostic of the specific cell type affected following injury since neurons and glia possess distinct proteins. For example, detection of glial proteins, peptides, fragments and derivatives thereof is diagnostic of glial cell damage. Examples of glial proteins, include, but not limited to: GFAP (P47819), Protein disulfide isomerase (PDI)—P04785, Neurocalcin delta, S100beta.

The ability to detect and monitor levels of these proteins after CNS injury provides enhanced diagnostic capability by allowing clinicians (1) to determine the level of injury severity in patients with various CNS injuries, (2) to monitor patients for signs of secondary CNS injuries that may elicit these cellular changes and (3) to monitor the effects of therapy by examination of these proteins in CSF or blood. Unlike other organ-based diseases where rapid diagnostics for surrogate biomarkers prove invaluable to the course of action taken to treat the disease, no such rapid, definitive diagnostic tests exist for traumatic or ischemic brain injury that might provide physicians with quantifiable neurochemical markers to help determine the seriousness of the injury, the anatomical and cellular pathology of the injury, and the implementation of appropriate medical management and treatment.

In an illustrative example, not meant to limit or construe the invention in any way, identification of which brain-specific and brain-enriched proteins are elevated in CSF following traumatic brain injury (TBI) is diagnostic, for example, of brain injury, the degree of brain injury, type of cellular damage and degree of cellular damage. Furthermore, detection of certain brain-specific and brain-enriched proteins, fragments and derivatives thereof, is diagnostic of the type and degree of cellular damage. For example, increased levels of a variety of brain-specific and brain-enriched proteins in the CSF 48 hours following injury, were detected. Specifically, elevated levels of the somal protein ubiquitin C-terminal hydrolase L1 (UCH-L1) the dendritic protein p24, and α-synuclein, a pre-synaptic protein were detected following injury.

In comparison to currently existing products, the invention provides several superior advantages and benefits. First, the identification of neuronal biomarkers provide more rapid and less expensive diagnosis of injury severity than existing diagnostic devices such as computed tomography (CT) and magnetic resonance imaging (MM). The invention also allows quantitative detection and high content assessment of damage to the CNS at a subcellular level (i.e. axonal versus dendritic). The invention also allows identification of the specific cell type affected (for example, neurons versus glia). In addition, levels of these brain-specific and brain-enriched proteins provides more accurate information regarding the level of injury severity than what is on the market.

In another preferred embodiment, nerve cell damage in a subject is analyzed by (a) providing a biological sample isolated from a subject suspected of having a damaged nerve cell; (b) detecting in the sample the presence or amount of at least one marker selected from one or more neural proteins; and (c) correlating the presence or amount of the marker with the presence or type of nerve cell damage in the subject. Preferably, neural cells, such as those cells that reside in the central and peripheral nerve systems, including nerve cells, glial cell, oligodendrocyte, microglia cells or neural stem cells) in in vitro culture or in situ in an animal subjects express higher levels of neural proteins ("neuronal specific or neuronally enriched" proteins; examples are outlined in Table 1) as compared to non-neuronal cells, such as cardiomyocytes, myocytes in skeletal muscles, hepatocytes, kidney cells and cells in testis. Preferably, the samples comprise neural cells, for example, a biopsy of a central nervous system or peripheral nervous system tissue are suitable biological samples for use in the invention. In addition, after injury to the nervous system (such as brain injury), the neural cell membrane is compromised, leading to the efflux of these neural proteins first into the extracellular fluid or space and to the cerebrospinal fluid and eventually in the circulating blood (as assisted by the compromised blood brain barrier) and other biofluids (e.g. urine, sweat, s saliva, etc.). Thus, other suitable biological samples include, but not limited to such cells or fluid secreted from these cells. Obtaining biological fluids such as cerebrospinal fluid, blood, plasma, serum, saliva and urine, from a subject is typically much less invasive and traumatizing than obtaining a solid tissue biopsy sample. Thus, samples, which are biological fluids, are preferred for use in the invention. CSF, in particular, is preferred for detecting nerve damage in a subject as it is in direct contact with the nervous system and is readily obtainable.

In a preferred embodiment, detection of nerve cell damage comprises detection of one or more biomarkers comprising: Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GABA-B-R2.

In another preferred embodiment, detection of neural damage comprises detection of one or more biomarkers comprising at least one biomarker from each neural cell type. The composition of biomarkers is diagnostic of neural injury, damage and/or neural disorders. The composition or panel of biomarkers comprises: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

A biological sample can be obtained from a subject by conventional techniques. For example, CSF can be obtained by lumbar puncture. Blood can be obtained by venipuncture, while plasma and serum can be obtained by fractionating whole blood according to known methods. Surgical techniques for obtaining solid tissue samples are well known in the art. For example, methods for obtaining a nervous system tissue sample are described in standard neurosurgery texts such as Atlas of Neurosurgery: Basic Approaches to Cranial and Vascular Procedures, by F. Meyer, Churchill Livingstone, 1999; Stereotactic and Image Directed Surgery of Brain Tumors, 1st ed., by David G. T. Thomas, WB Saunders Co., 1993; and Cranial Microsurgery: Approaches and Techniques, by L. N. Sekhar and E. De Oliveira, 1st ed., Thieme Medical Publishing, 1999. Methods for obtaining and analyzing brain tissue are also described in Belay et al., *Arch. Neurol.* 58: 1673-1678 (2001); and Seijo et al., *J. Clin. Microbiol.* 38: 3892-3895 (2000).

Any animal that expresses the neural proteins, such as for example, those listed in Table 1, can be used as a subject from which a biological sample is obtained. Preferably, the subject is a mammal, such as for example, a human, dog, cat, horse, cow, pig, sheep, goat, primate, rat, mouse and other vertebrates such as fish, birds and reptiles. More preferably, the subject is a human. Particularly preferred are subjects suspected of having or at risk for developing traumatic or non-traumatic nervous system injuries, such as victims of brain injury caused by traumatic insults (e.g. gunshots wounds, automobile accidents, sports accidents, shaken baby syndrome), ischemic events (e.g. stroke, cerebral hemorrhage, cardiac arrest), spinal cord injury, neurodegenerative disorders (such as Alzheimer's, Huntington's, and Parkinson's diseases; Prion-related disease; other forms of dementia, and spinal cord degeneration), epilepsy, substance abuse (e.g., from amphetamines, methamphetamine/Speed, Ecstasy/MDMA, or ethanol and cocaine), and peripheral nervous system pathologies such as diabetic neuropathy, chemotherapy-induced neuropathy and neuropathic pain, peripheral nerve damage or atrophy (ALS), multiple sclerosis (MS).

Subcellular neuronal markers
Axonal Proteins

α II spectrin (and SPDB) -1
NF-68 (NF-L) - 2
Tau - 3
β II, III spectrin
NF-200 (NF-H)
NF-160 (NF-M)
Amyloid precursor protein
α internexin
Dendritic Proteins betaIII-tubulin - 1
p24 microtubule-associated protein - 2
alpha-Tubulin (P02551)
beta-Tubulin (P04691)
MAP-2A/B - 3
MAP-2C -3
Stathmin - 4
Dynamin-1 (P21575)
Phocein
Dynactin (Q13561)
Vimentin (P31000)
Dynamin
Profilin
Cofilin 1,2
Somal Proteins UCH-L1 (Q00981) - 1
Gyocogen phosphorylase-BB - 2
PEBP (P31044)
NSE (P07323)
CK-BB (P07335)
Thy 1.1
Prion protein
Huntingtin
14-3-3 proteins (e.g. 14-3-3-epsolon (P42655))
SM22-α
Calgranulin AB
alpha-Synuclein (P37377)
beta-Synuclein (Q63754)
HNP 22
Neural nuclear proteins NeuN - 1
S/G(2) nuclear autoantigen (SG2NA)
Huntingtin
Presynaptic Proteins Synaptophysin - 1
Synaptotagmin (P21707)
Synaptojanin-1 (Q62910)
Synaptojanin-2
Synapsin1 (Synapsin-Ia)
Synapsin2 (Q63537)
Synapsin3
GAP43
Bassoon(NP_003449)
Piccolo (aczonin) (NP_149015)
Syntaxin
CRMP1, 2
Amphiphysin -1 (NP_001626)
Amphiphysin -2 (NP_647477)
Post-Synaptic Proteins PSD95 - 1
NMDA-receptor (and all subtypes) -2
PSD93
AMPA-kainate receptor (all subtypes)
mGluR (all subtypes)
Calmodulin dependent protein kinase II (CAMPK)-alpha, beta, gamma
CaMPK-IV
SNAP-25
a-/b-SNAP
Nervous Cell subtype Biomarkers

Myelin-Oligodendrocyte

Myelin basic protein (MBP) and fragments
Myelin proteolipid protein (PLP)
Myelin Oligodendrocyte specific protein (MOSP)
Myelin Oligodendrocyte glycoprotein (MOG)
myelin associated protein (MAG)
Oligodendrocyte NS-1 protein
Glial Protein Biomarkers GFAP (P47819)
Protein disulfide isomerase (PDI) - P04785
Neurocalcin delta
S100beta
Microglia protein Biomarkers Iba1
OX-42
OX-8
OX-6
ED-1
PTPase (CD45)
CD40; CD68
CD11b
Fractalkine (CX3CL1) and Fractalkine receptor (CX3CR1)
5-d-4 antigen
Schwann cell markers Schwann cell myelin protein
Glia Scar Tenascin
Anatomical brain biomarkers (CNS + PNS)
Hippocampus Stathmin,
Hippocalcin
SCG10
Cerebellum Purkinje cell protein-2 (Pcp2)
Calbindin D9K,
Calbindin D28K (NP_114190)
Cerebellar CaBP, spot 35
Cerebrocortex Cortexin-1. P60606
H-2Z1 gene product
Thalamus CD15 (3-fucosyl-N-acetyl-lactosamine) epitope
Hypothalamus Orexin receptors (OX-1R and OX-2R)- appetite
Orexins (hypothalamus-specific peptides)
Corpus callosum MBP,
MOG,
PLP
MAG
Spinal Cord Schwann cell myelin protein
Striatum Striatin
Rhes (Ras homolog enriched in striatum)
Peripheral ganglia Gadd45a
Peripherial nerve fiber(sensory + motor)

Peripherin
Peripheral myelin protein 22 (AAH91499)
Other Neuron-specific proteins PH8 (S Serotonergic Dopaminergic
PEP-19, a neuron-specific protein Neurocalcin (NC),
a neuron-specific EF-hand Ca2+-binding protein
Encephalopsin
Striatin
SG2NA
Zinedin,
Recoverin
Visinin
Neuron Subtypes based on Neurotransmitter receptors and transporters
Neurotransmitter Receptors NMDA receptor subunits (e.g. NR1A2B)
Glutamate receptor subunits (AMPA, Kainate receptors (e.g. GluR1, GluR4)
beta-adrenoceptor subtypes (e.g. beta(2))
Alpha-adrenoceptors subtypes (e.g. alpha(2c))
GABA receptors (e.g. GABA(B))
Metabotropic glutamate receptor (e.g. mGluR3)
5-HT serotonin receptors (e.g. 5-HT(3))
Dopamine receptors (e.g. D4)
Muscarinic Ach receptors (e.g. M1)
Nicotinic Acetylcholine Receptor (e.g. alpha-7)
Neurotransmitter Transporters Norepinephrine Transporter (NET)
Dopamine transporter (DAT)
Serotonin transporter (SERT)
Vesicular transporter proteins (VMAT1 and VMAT2)
GABA transporter vesicular inhibitory amino acid transporter
(VIAAT/VGAT)
Glutamate Transporter (e.g. GLT1)
Vesicular acetylcholine transporter
Vesicular Glutamate Transporter 1
[VGLUT1; BNPI] and VGLUT2
Choline transporter, (e.g. CHT1)
Neuron Subtypes based on Neurotransmitter system
Cholinergic Biomarkers Acetylcholine Esterase
Choline acetyltransferase [ChAT]
Dopaminergic Biomarkers Tyrosine Hydroxylase (TH)
Phospho-TH
DARPP32
Noradrenergic Biomarkers
Dopamine beta-hydroxylase (DbH)
Adrenergic Biomarkers Phenylethanolamine N-methyltransferase (PNMT)
Serotonergic Biomarkers
Tryptophan Hydroxylase (TrH)
Glutamatergic Biomarkers Glutaminase
Glutamine synthetase
GABAergic Biomarkers GABA transaminase [GABAT])
GABA-B-R2

As described above, the invention provides the step of correlating the presence or amount of one or more neural protein(s) with the severity and/or type of nerve cell injury. The amount of a neural proteins, peptides, fragments, derivatives or the modified forms, thereof, directly relates to severity of nerve tissue injury as more severe injury damages a greater number of nerve cells which in turn causes a larger amount of neural protein(s) to accumulate in the biological sample (e.g., CSF). Whether a nerve cell injury triggers an apoptotic, oncotic (necrotic) or type 2 (autophagic) cell death, can be determined by examining the unique proteins released into the biofluid in response to different cell death phenotype. The unique proteins are detected from the many cell types that comprise the nervous system. For example, astroglia, oligodendrocytes, microglia cells, Schwann cells, fibroblast, neuroblast, neural stem cells and mature neurons. Furthermore, mature neurons are differentiated into dedicated subtype fusing a primary neural transmitter such as cholinergic (nicotinic and mucarinic), glutamatergic, gabaergic, serotonergic, dopaminergic. Each of this neuronal subtype express unique neural proteins such as those dedicated for the synthesis, metabolism and transporter and receptor of each unique neurotransmitter system (Table 1). Lastly, within a single nerve cell, there are subcellularly defined structures matched with unique neural proteins (dendritic, axonal, myelin sheath, presynaptic terminal and postsynaptic density). By monitoring the release of proteins unique to each of these regions, subcellular damage can be monitored and defined after brain injury (FIG. 2).

The biomarkers of the invention can be detected in a sample by any means. Methods for detecting the biomarkers are described in detail in the materials and methods and Examples which follow. For example, immunoassays, include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen (i.e. neural biomarker), coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Identification of New Markers and Quantitation of Markers

In a preferred embodiment, a biological sample is obtained from a patient with neural injury. Biological samples comprising biomarkers from other patients and control subjects (i.e. normal healthy individuals of similar age, sex, physical condition) are used as comparisons. Biological samples are extracted as discussed above. Preferably, the sample is prepared prior to detection of biomarkers. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In one embodiment, a sample can be pre-fractionated according to size of proteins in a sample using size exclusion chromatography. For a biological sample wherein the amount of sample available is small, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by immunoassays, gas phase ion spectrometry, and the like, for the detection of markers.

In another embodiment, a sample can be pre-fractionated by anion exchange chromatography. Anion exchange chromatography allows pre-fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomarkers in a sample that are more negatively charged from other types of biomarkers. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be pre-fractionated by heparin chromatography. Heparin chromatography allows pre-fractionation of the markers in a sample also on the basis of affinity interaction with heparin and charge characteristics. Heparin, a sulfated mucopolysaccharide, will bind markers with positively charged moieties and a sample can be sequentially eluted with eluants having different pH's or salt concentrations. Markers eluted with an eluant having a low pH are more likely to be weakly positively charged. Markers eluted with an eluant having a high pH are more likely to be strongly positively charged. Thus, heparin chromatography also reduces the complexity of a sample and separates markers according to their binding characteristics.

In yet another embodiment, a sample can be pre-fractionated by isolating proteins that have a specific characteristic, e.g. are glycosylated. For example, a CSF sample can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomarkers from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomarkers. In this embodiment, the sample is applied to a first adsorbent on the probe, which is subsequently washed with an eluant. Markers that do not bind to the first adsorbent are removed with an eluant. The markers that are in the fraction can be applied to a second adsorbent on the probe, and so forth. The advantage of performing sequential extraction on a gas phase ion spectrometer probe is that markers that bind to various adsorbents at every stage of the sequential extraction protocol can be analyzed directly using a gas phase ion spectrometer.

In yet another embodiment, biomarkers in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomarkers, including one or more markers. See, e.g., Jungblut and Thiede, *Mass Spectr. Rev.* 16:145-162 (1997). The two-dimensional gel electrophoresis can be performed using methods known in the art. See, e.g., Deutscher ed., *Methods In Enzymology* vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one dimensional array is further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI.

Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In yet another embodiment, high performance liquid chromatography (HPLC) can be used to separate a mixture of biomarkers in a sample based on their different physical properties, such as polarity, charge and size. HPLC instruments typically consist of a reservoir of mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt).

After preparation, biomarkers in a sample are typically captured on a substrate for detection. Traditional substrates include antibody-coated 96-well plates or nitrocellulose membranes that are subsequently probed for the presence of proteins. Preferably, the biomarkers are identified using immunoassays as described above. However, preferred methods also include the use of biochips. Preferably the biochips are protein biochips for capture and detection of proteins. Many protein biochips are described in the art. These include, for example, protein biochips produced by Packard BioScience Company (Meriden Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture reagent bound there. The capture reagent can be a biological molecule, such as a polypeptide or a nucleic acid, which captures other biomarkers in a specific manner. Alternatively, the capture reagent can be a chromatographic material, such as an anion exchange material or a hydrophilic material. Examples of such protein biochips are described in the following patents or patent applications: U.S. Pat. No. 6,225,047 (Hutchens and Yip, "Use of retentate chromatography to generate difference maps," May 1, 2001), International publication WO 99/51773 (Kuimelis and Wagner, "Addressable protein arrays," Oct. 14, 1999), International publication WO 00/04389 (Wagner et al., "Arrays of protein-capture agents and methods of use thereof," Jul. 27, 2000), International publication WO 00/56934 (Englert et al., "Continuous porous matrix arrays," Sep. 28, 2000).

In general, a sample containing the biomarkers is placed on the active surface of a biochip for a sufficient time to allow binding. Then, unbound molecules are washed from the surface using a suitable eluant. In general, the more stringent the eluant, the more tightly the proteins must be bound to be retained after the wash. The retained protein biomarkers now can be detected by appropriate means.

Analytes captured on the surface of a protein biochip can be detected by any method known in the art. This includes, for example, mass spectrometry, fluorescence, surface plasmon resonance, ellipsometry and atomic force microscopy. Mass spectrometry, and particularly SELDI mass spectrometry, is a particularly useful method for detection of the biomarkers of this invention.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry, or MALDI-MS, is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry. MALDI-MS is useful for detecting the biomarkers of this invention if the complexity of a sample has been substantially reduced using the preparation methods described above.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI is described, for example, in: U.S. Pat. No. 5,719,060 ("Method and Apparatus for Desorption and Ionization of Analytes," Hutchens and Yip, Feb. 17, 1998,) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of markers or other substances will typically involve detection of signal intensity. This, in turn, can reflect the quantity and character of markers bound to the substrate. Any of the components of a mass spectrometer (e.g., a desorption source, a mass analyzer, a detector, etc.) can be combined with other suitable components described herein or others known in the art in embodiments of the invention.

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

To prepare an antibody that specifically binds to a marker, purified markers or their nucleic acid sequences can be used. Nucleic acid and amino acid sequences for markers can be obtained by further characterization of these markers. For example, each marker can be peptide mapped with a number of enzymes (e.g., trypsin, V8 protease, etc.). The molecular weights of digestion fragments from each marker can be used to search the databases, such as SwissProt database, for sequences that will match the molecular weights of digestion fragments generated by various enzymes. Using this method, the nucleic acid and amino acid sequences of other markers can be identified if these markers are known proteins in the databases.

Alternatively, the proteins can be sequenced using protein ladder sequencing. Protein ladders can be generated by, for example, fragmenting the molecules and subjecting fragments to enzymatic digestion or other methods that sequentially remove a single amino acid from the end of the fragment. Methods of preparing protein ladders are described, for example, in International Publication WO 93/24834 (Chait et al.) and U.S. Pat. No. 5,792,664 (Chait et al.). The ladder is then analyzed by mass spectrometry. The difference in the masses of the ladder fragments identify the amino acid removed from the end of the molecule.

If the markers are not known proteins in the databases, nucleic acid and amino acid sequences can be determined with knowledge of even a portion of the amino acid sequence of the marker. For example, degenerate probes can be made based on the N-terminal amino acid sequence of the marker. These probes can then be used to screen a genomic or cDNA library created from a sample from which a marker was initially detected. The positive clones can be identified, amplified, and their recombinant DNA sequences can be subcloned using techniques which are well known. See, e.g., *Current Protocols for Molecular Biology* (Ausubel et al., Green Publishing Assoc. and Wiley-Interscience 1989) and *Molecular Cloning: A Laboratory Manual*, 3rd Ed. (Sambrook et al., Cold Spring Harbor Laboratory, N Y 2001).

Using the purified markers or their nucleic acid sequences, antibodies that specifically bind to a marker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

After the antibody is provided, a marker can be detected and/or quantified using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (MA), a Western blot assay, or a slot blot assay. These methods are also described in, e.g., *Methods in Cell Biology: Antibodies in Cell Biology*, volume 37 (Asai, ed. 1993); *Basic and Clinical Immunology* (Stites & Terr, eds., 7th ed. 1991); and Harlow & Lane, supra. The detection and quantitation of biomarkers is described in detail in the Examples which follow.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological fluid sample taken from a subject. Examples of biological fluid samples include cerebrospinal fluid, blood, serum, plasma, neuronal cells, tissues, urine, tears, saliva etc. In a preferred embodiment, the biological fluid comprises cerebrospinal fluid. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid in the diagnosis of spinal injury, brain injury, the degree of injury, neural injury due to neuronal disorders, alcohol and drug abuse, fetal injury due to alcohol and/or drug abuse by pregnant mothers, etc. In another example, the methods for detection of the markers can be used to monitor responses in a subject to treatment. In another example, the methods for detecting markers can be used to assay for and to identify compounds that modulate expression of these markers in vivo or in vitro.

Data generated by desorption and detection of markers can be analyzed using any suitable means. In one embodiment, data is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a CSF protein) may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular mass of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., normal, healthy subjects in whom neural injury is undetectable).

Diagnosis of Neural Injury

In another aspect, the invention provides methods for aiding a human neural injury and/or neural disorder diagnosis using one or more markers. For example, proteins identified in Table 1, peptides, fragments or derivatives thereof. These markers can be used singularly or in combination with other markers in any set, for example, axonal and dendritic. The markers are differentially present in samples of a human patient, for example a TBI patient, and a normal subject in whom neural injury is undetectable. For example, some of the markers are expressed at an elevated level and/or are present at a higher frequency in human patients with neural injury and/or neuronal disorders than in normal subjects. Therefore, detection of one or more of these markers in a person would provide useful information regarding the probability that the person may have neural injury and/or neuronal disorder.

Nervous system diseases, neuronal disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

Accordingly, embodiments of the invention include methods for aiding human neural injury and/or neuronal disorders, wherein the method comprises: (a) detecting at least one marker in a sample, wherein the marker is selected from any one of the markers listed in Table 1, peptides, fragments and derivatives thereof; and (b) correlating the detection of the marker or markers with a probable diagnosis of human neural injury and/or neuronal disorder. The correlation may take into account the amount of the marker or markers in the sample compared to a control amount of the marker or markers (up or down regulation of the marker or markers) (e.g., in normal subjects in whom human neural injury is undetectable). The correlation may take into account the presence or absence of the markers in a test sample and the frequency of detection of the same markers in a control. The correlation may take into account both of such factors to facilitate determination of whether a subject has neural injury, the degree of severity of the neural injury, and subcellular location of the injury, or not.

In a preferred embodiment, the method of diagnosing and detecting neural injury and/or neural disorders comprises detecting one or more biomarkers: Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G (2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin 1 (Synapsin-Ia), Synapsin2 (Q63537), Synapsin3, GAP43, Bassoon(NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha(2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GABA-B-R2.

In another preferred embodiment, the method of diagnosing and detecting neural injury and/or neural disorders comprises detecting at least one biomarker from each neural cell type. The composition of biomarkers is diagnostic of neural injury, damage and/or neural disorders. The composition comprises: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

Any suitable samples can be obtained from a subject to detect markers. Preferably, a sample is a cerebrospinal fluid sample from the subject. If desired, the sample can be prepared as described above to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography and the like. Sample preparations, such as pre-fractionation protocols, is optional and may not be necessary to enhance detectability of markers depending on the methods of detection used. For example, sample preparation may be unnecessary if antibodies that specifically bind markers are used to detect the presence of markers in a sample.

Any suitable method can be used to detect a marker or markers in a sample. For example, an immunoassay or gas phase ion spectrometry can be used as described above. Using these methods, one or more markers can be detected. Preferably, a sample is tested for the presence of a plurality of markers. Detecting the presence of a plurality of markers, rather than a single marker alone, would provide more information for the diagnostician. Specifically, the detection of a plurality of markers in a sample would increase the percentage of true positive and true negative diagnoses and would decrease the percentage of false positive or false negative diagnoses.

The detection of the marker or markers is then correlated with a probable diagnosis of neural injury and/or neuronal disorders. In some embodiments, the detection of the mere presence or absence of a marker, without quantifying the amount of marker, is useful and can be correlated with a probable diagnosis of neural injury and/or neuronal disorders. For example, neural proteins, fragments or derivatives thereof, such as for example, axonal proteins—NF-200 (NF-H), NF-160 (NF-M), NF-68 (NF-L); can be more frequently detected in patients with neuronal injury than in normal subjects.

In other embodiments, the detection of markers can involve quantifying the markers to correlate the detection of markers with a probable diagnosis of neural injury, degree of severity of neural injury, diagnosis of neural disorders and the like. Thus, if the amount of the markers detected in a subject being tested is higher compared to a control amount, then the subject being tested has a higher probability of having such injuries and/or neural disorders.

Similarly, in another embodiment, the detection of markers can further involve quantifying the markers to correlate the detection of markers with a probable diagnosis of neural injury, degree of severity of neural injury, diagnosis of neural disorders and the like, wherein the markers are present in lower quantities in CSF or blood serum samples from patients than in blood serum samples of normal subjects. Thus, if the amount of the markers detected in a subject being tested is lower compared to a control amount, then the subject being tested has a higher probability of having neural injury and/or neural disorder.

When the markers are quantified, it can be compared to a control. A control can be, e.g., the average or median amount of marker present in comparable samples of normal subjects in whom neural injury and/or neural disorders, is undetectable. The control amount is measured under the same or substantially similar experimental conditions as in measuring the test amount. For example, if a test sample is obtained from a subject's cerebrospinal fluid and/or blood serum sample and a marker is detected using a particular probe, then a control amount of the marker is preferably determined from a serum sample of a patient using the same probe. It is preferred that the control amount of marker is determined based upon a significant number of samples from normal subjects who do not have neural injury and/or neuronal disorders so that it reflects variations of the marker amounts in that population.

Data generated by mass spectrometry can then be analyzed by a computer software. The software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and human neural injury and determines the closeness of fit between the two signals. The software also can include code indicating which the test sample is closest to, thereby providing a probable diagnosis.

Production of Antibodies to Detect Neural Biomarkers

Neural biomarkers obtained from samples in patients suffering from varying neural injuries, degrees of severity of injury, neuronal disorders and the like, can be prepared as described above. Furthermore, neural biomarkers can be subjected to enzymatic digestion to obtain fragments or peptides of the biomarkers for the production of antibodies to different antigenic epitopes that can be present in a peptide versus the whole protein. Antigenic epitopes are useful, for example, to raise antibodies, including monoclonal antibodies, that specifically bind the epitope. Antigenic epitopes can be used as the target molecules in immunoassays. (See, for instance, Wilson et al., Cell 37:767-778 (1984); Sutcliffe et al., Science 219:660-666 (1983)).

In a preferred embodiment, antibodies are directed to epitopes (specifically bind) of biomarkers Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G (2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon(NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha(2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GAB A-B-R2.

In another preferred embodiment, the antibodies of the invention bind to at least one biomarker from each neural cell type. The composition of biomarkers is diagnostic of neural injury, damage and/or neural disorders. The composition comprises: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

Neural biomarker epitopes can be used, for example, to induce antibodies according to methods well known in the art. (See, for instance, Sutcliffe et al., supra; Wilson et al., supra; Chow et al., *Proc. Natl. Acad. Sci. USA* 82:910-914; and Bittle et al., *J. Gen. Virol.* 66:2347-2354 (1985). Neural polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 3 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.,* 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Nucleic acids neural biomarker epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, *Proc. Natl. Acad. Sci. USA* 88:8972-8976). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

The antibodies of the present invention may be generated by any suitable method known in the art. The antibodies of the present invention can comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988), which is hereby incorporated herein by reference in its entirety). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides as may be described herein.

Typically, the immunizing agent and/or adjuvant will be injected in the mammal by multiple subcutaneous or intraperitoneal injections, though they may also be given intramuscularly, and/or through IV. The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivatizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention can also comprise monoclonal antibodies. Monoclonal antibodies may be prepared using hybridoma methods, such as those described by Kohler and Milstein, *Nature,* 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, *Immunology Today* 4:72; Cole et al., 1983, *Proc. Natl. Acad. Sci. USA* 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include neural polypeptides, fragments or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred throughout the specification, human myeloma and mouse-human heteromyeloma cell lines also have been described for the production of human monoclonal antibodies (Kozbor, *J. Immunol.,* 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the neural polypeptides of the present invention. Preferably, the binding specificity of monoclonal antibodies produced by the hybridoma cells is determined by immunoprecipitation or by an in vitro binding assay, such as radioimmunoassay (MA) or enzyme-linked immunoadsorbant assay (ELISA). Such techniques are known in the art and within the skill of the artisan. The binding affinity of the monoclonal antibody can, for example, be determined by the Scatchard analysis of Munson and Pollart, *Anal. Biochem.,* 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells.

Methods for producing and screening for specific antibodies using hybridoma technology are routine and well known in the art. In a non-limiting example, mice can be immunized with a biomarker polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. The antibodies detecting neural biomarkers, peptides and derivatives thereof, can be used in immunoassays and other methods to identify new neural biomarkers and for use in the diagnosis of neural injury, degree of severity of injury and/or neurological disorders.

Other methods can also be used for the large scale production of neural biomarker specific antibodies. For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

The antibodies of the present invention have various utilities. For example, such antibodies may be used in diagnostic assays to detect the presence or quantification of the polypeptides of the invention in a sample. Such a diagnostic assay can comprise at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., *Anal Biochem.*, 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as $^{2}$H, $^{14}$C, $^{32}$P, or $^{125}$I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., *Nature*, 144:945 (1962); David et al., *Biochem.*, 13:1014 (1974); Pain et al., *J. Immunol. Methods*, 40:219(1981); and Nygren, *J. Histochem. and Cytochem.*, 30:407 (1982).

Kits

In yet another aspect, the invention provides kits for aiding a diagnosis of neural injury, degree of severity of injury, subcellular localization and/or neuronal disorders, wherein the kits can be used to detect the markers of the present invention. For example, the kits can be used to detect any one or more of the markers described herein, which markers are differentially present in samples of a patient and normal subjects. The kits of the invention have many applications. For example, the kits can be used to differentiate if a subject has axonal injury versus, for example, dendritic, or has a negative diagnosis, thus aiding neuronal injury diagnosis. In another example, the kits can be used to identify compounds that modulate expression of one or more of the markers in in vitro or in vivo animal models to determine the effects of treatment.

In one embodiment, a kit comprises (a) an antibody that specifically binds to a marker; and (b) a detection reagent. Such kits can be prepared from the materials described above, and the previous discussion regarding the materials (e.g., antibodies, detection reagents, immobilized supports, etc.) is fully applicable to this section and will not be repeated. Optionally, the kit may further comprise pre-fractionation spin columns. In some embodiments, the kit may further comprise instructions for suitable operation parameters in the form of a label or a separate insert.

In another embodiment, the kit comprises (a) a panel or composition of biomarkers (b) a detecting agent. The panel or composition of biomarkers included in a kit include at least one biomarker and/or a plurality of biomarkers in order to diagnose in vivo location of neural injury. These biomarkers include: Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP 22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GAB A-B-R2.

In another preferred embodiment, the panel of biomarkers in a kit at least one biomarker from each neural cell type. The composition of biomarkers is diagnostic of neural injury, damage and/or neural disorders. The composition comprises: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

In another preferred embodiment, the antibodies in a kit are specific for a panel of biomarkers and one or more antibodies can be used. Antibodies are specific for biomarkers: Axonal Proteins: α II spectrin (and SPDB)-1, NF-68 (NF-L)-2, Tau-3, α II, III spectrin, NF-200 (NF-H), NF-160 (NF-M), Amyloid precursor protein, α internexin; Dendritic Proteins: beta III-tubulin-1, p24 microtubule-associated protein-2, alpha-Tubulin (P02551), beta-Tubulin (P04691), MAP-2A/B-3, MAP-2C-3, Stathmin-4, Dynamin-1 (P21575), Phocein, Dynactin (Q13561), Vimentin (P31000), Dynamin, Profilin, Cofilin 1,2; Somal Proteins: UCH-L1 (Q00981)-1, Glycogen phosphorylase-BB-2, PEBP (P31044), NSE (P07323), CK-BB (P07335), Thy 1.1, Prion protein, Huntingtin, 14-3-3 proteins (e.g. 14-3-3-epsolon (P42655)), SM22-α, Calgranulin AB, alpha-Synuclein (P37377), beta-Synuclein (Q63754), HNP_22; Neural nuclear proteins: NeuN-1, S/G(2) nuclear autoantigen (SG2NA), Huntingtin; Presynaptic Proteins: Synaptophysin-1, Synaptotagmin (P21707), Synaptojanin-1 (Q62910), Synaptojanin-2, Synapsin1 (Synapsin-Ia), Synapsin2 (Q63537), Synapsin3, GAP43, Bassoon (NP_003449), Piccolo (aczonin) (NP_149015), Syntaxin, CRMP1, 2, Amphiphysin-1 (NP_001626), Amphiphysin-2 (NP_647477); Post-Synaptic Proteins: PSD95-1, NMDA-receptor (and all subtypes)-2, PSD93, AMPA-kainate receptor (all subtypes), mGluR (all subtypes), Calmodulin dependent protein kinase II (CAMPK)-alpha, beta, gamma, CaMPK-IV, SNAP-25, a-/b-SNAP; Myelin-Oligodendrocyte: Myelin basic protein (MBP) and fragments, Myelin proteolipid protein (PLP), Myelin Oligodendrocyte specific protein (MOSP), Myelin Oligodendrocyte glycoprotein (MOG), myelin associated protein (MAG), Oligodendrocyte NS-1 protein; Glial Protein Biomarkers: GFAP (P47819), Protein disulfide isomerase (PDI)-P04785, Neurocalcin delta, S100beta; Microglia protein Biomarkers: Iba1, OX-42, OX-8, OX-6, ED-1, PTPase (CD45), CD40, CD68, CD11b, Fractalkine (CX3CL1) and Fractalkine receptor (CX3CR1), 5-d-4 antigen; Schwann cell markers: Schwann cell myelin protein; Glia Scar: Tenascin; Hippocampus: Stathmin, Hippocalcin, SCG10; Cerebellum: Purkinje cell protein-2 (Pcp2), Calbindin D9K, Calbindin D28K (NP_114190), Cerebellar CaBP, spot 35; Cerebrocortex: Cortexin-1 (P60606), H-2Z1 gene product; Thalamus: CD15 (3-fucosyl-N-acetyl-lactosamine) epitope; Hypothalamus: Orexin receptors (OX-1R and OX-2R)-appetite, Orexins (hypothalamus-specific peptides); Corpus callosum: MBP, MOG, PLP, MAG; Spinal Cord: Schwann cell myelin protein; Striatum: Striatin, Rhes (Ras homolog enriched in striatum); Peripheral ganglia: Gadd45a; Peripherial nerve fiber(sensory+motor): Peripherin, Peripheral myelin protein 22 (AAH91499); Other Neuron-specific proteins: PH8 (S Serotonergic Dopaminergic, PEP-19, Neurocalcin (NC), a neuron-specific EF-hand $Ca^{2+}$-binding protein, Encephalopsin, Striatin, SG2NA, Zinedin, Recoverin, Visinin; Neurotransmitter Receptors: NMDA receptor subunits (e.g. NR1A2B), Glutamate receptor subunits (AMPA, Kainate receptors (e.g. GluR1, GluR4), beta-adrenoceptor subtypes (e.g. beta(2)), Alpha-adrenoceptors subtypes (e.g. alpha (2c)), GABA receptors (e.g. GABA(B)), Metabotropic glutamate receptor (e.g. mGluR3), 5-HT serotonin receptors (e.g. 5-HT(3)), Dopamine receptors (e.g. D4), Muscarinic Ach receptors (e.g. M1), Nicotinic Acetylcholine Receptor (e.g. alpha-7); Neurotransmitter Transporters: Norepinephrine Transporter (NET), Dopamine transporter (DAT), Serotonin transporter (SERT), Vesicular transporter proteins (VMAT1 and VMAT2), GABA transporter vesicular inhibitory amino acid transporter (VIAAT/VGAT), Glutamate Transporter (e.g. GLT1), Vesicular acetylcholine transporter, Vesicular Glutamate Transporter 1, [VGLUT1; BNPI] and VGLUT2, Choline transporter, (e.g. CHT1); Cholinergic Biomarkers: Acetylcholine Esterase, Choline acetyltransferase [ChAT]; Dopaminergic Biomarkers: Tyrosine Hydroxylase (TH), Phospho-TH, DARPP32; Noradrenergic Biomarkers: Dopamine beta-hydroxylase (DbH); Adrenergic Biomarkers: Phenylethanolamine N-methyltransferase (PNMT); Serotonergic Biomarkers: Tryptophan Hydroxylase (TrH); Glutamatergic Biomarkers: Glutaminase, Glutamine synthetase; GABAergic Biomarkers: GABA transaminase [GABAT]), GAB A-B-R2.

In another preferred embodiment, the antibodies are specific for at least one biomarker from each neural cell type. The composition of biomarkers is diagnostic of neural injury, damage and/or neural disorders. The antibodies bind to: α II spectrin, SPDB-1, NF-68, NF-L-2, Tau-3, βIII-tubulin-1, p24 microtubule-associated protein-2, UCH-L1 (Q00981)-1, Glycogen phosphorylase-BB-2, NeuN-1, Synaptophysin-1, synaptotagmin (P21707), Synaptojanin-1 (Q62910), Synaptojanin-2, PSD95-1, NMDA-receptor-2 and subtypes, myelin basic protein (MBP) and fragments, GFAP (P47819), Iba1, OX-42, OX-8, OX-6, ED-1, Schwann cell myelin protein, tenascin, stathmin, Purkinje cell protein-2 (Pcp2), Cortexin-1 (P60606), Orexin receptors (OX-1R, OX-2R), Striatin, Gadd45a, Peripherin, peripheral myelin protein 22 (AAH91499), and Neurocalcin (NC).

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Optionally, the kit may further comprise a standard or control information so that the test sample can be compared with the control information standard to determine if the test amount of a marker detected in a sample is a diagnostic amount consistent with a diagnosis of neural injury, degree of severity of the injury, subcellular localization, neuronal disorder and/or effect of treatment on the patient.

In another embodiment, a kit comprises: (a) a substrate comprising an adsorbent thereon, wherein the adsorbent is suitable for binding a marker, and (b) instructions to detect the marker or markers by contacting a sample with the adsorbent and detecting the marker or markers retained by the adsorbent. In some embodiments, the kit may comprise an eluant (as an alternative or in combination with instructions) or instructions for making an eluant, wherein the combination of the adsorbent and the eluant allows detection of the markers using gas phase ion spectrometry. Such kits can be prepared from the materials described above, and the previous discussion of these materials (e.g., probe substrates, adsorbents, washing solutions, etc.) is fully applicable to this section and will not be repeated.

In another embodiment, the kit may comprise a first substrate comprising an adsorbent thereon (e.g., a particle functionalized with an adsorbent) and a second substrate onto which the first substrate can be positioned to form a probe which is removably insertable into a gas phase ion spectrometer. In other embodiments, the kit may comprise a single substrate which is in the form of a removably insertable probe with adsorbents on the substrate. In yet another embodiment, the kit may further comprise a pre-fractionation spin column (e.g., Cibacron blue agarose column, anti-HSA agarose column, size exclusion column, Q-anion exchange spin column, single stranded DNA column, lectin column, etc.).

Optionally, the kit can further comprise instructions for suitable operational parameters in the form of a label or a separate insert. For example, the kit may have standard instructions informing a consumer how to wash the probe after a sample is contacted on the probe. In another example, the kit may have instructions for pre-fractionating a sample to reduce complexity of proteins in the sample. In another example, the kit may have instructions for automating the fractionation or other processes.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

EXAMPLES

Materials and Methods
Abbreviations:
AEBSF, 4-(2-aminoethyl)-benzenesulfonylflouride; EDTA, ethylenediaminetetraacetic acid; EGTA, ethylenebis(oxyethylenenitrilo) tetra acetic acid; DMEM, Dulbecco's modified Eagle's medium; BSA, bovine serum albumin; DPBS, Dulbecco's phosphate buffered saline; DTT, dithiothreitol; FDA, fluorescein diacetate; GFAP, glial fibrillary acid protein; HBSS, Hanks' balanced salt solution; MAP-2, microtubule associated protein-2; PI, propidium iodide; PMSF, phenylmethylsulfonyl fluoride; SDS, sodium dedocyl sulfate; TEMED, N,N,N',N'-tetramethyletheylenediamine; Calpinh-II, calpain inhibitor II (N-acetyl-Leu-Leu-methioninal); Z-D-DCB, pan-caspase inhibitor (carbobenzoxy-Asp-$CH_2$—OC (O)-2-6-dichlorobenzene); PBS, phosphate buffered saline; TLCK, Nα-p-tosyl-L-Lysine chloro methyl; TPCK, N-tosyl-L-phenylalanine chloromethyl ketone.

Surgical Procedures
Controlled cortical impact traumatic brain injury. A cortical impact injury device was used to produce TBI in rodents. Cortical impact TBI results in cortical deformation within the vicinity of the impactor tip associated with contusion, and neuronal and axonal damage that is constrained in the hemisphere ipsilateral to the site of injury. Adult male (280-300 g) Sprague-Dawley rats (Harlan; Indianapolis, Ind.) were initially anesthetized with 4% isoflurane in a carrier gas of 1:1 $O_2/N_2O$ (4 min.) followed by maintenance anesthesia of 2.5% isoflurane in the same carrier gas. Core body temperature was monitored continuously by a rectal thermistor probe and maintained at 37±1° C. by placing an adjustable temperature controlled heating pad beneath the rats. Animals were mounted in a stereotactic frame in a prone position and secured by ear and incisor bars.

A midline cranial incision was made, the soft tissues were reflected, and a unilateral (ipsilateral to site of impact) craniotomy (7 mm diameter) was performed adjacent to the central suture, midway between bregma and lambda. The dura mater was kept intact over the cortex. Brain trauma in rats was produced by impacting the right cortex (ipsilateral cortex) with a 5 mm diameter aluminum impactor tip (housed in a pneumatic cylinder) at a velocity of 3.5 m/s with a 2.0 mm compression and 150 ms dwell time (compression duration). Velocity was controlled by adjusting the pressure (compressed $N_2$) supplied to the pneumatic cylinder. Velocity and dwell time were measured by a linear velocity displacment transducer (Lucas Shaevitz™ model 500 HR; Detroit, Mich.) that produces an analogue signal that was recorded by a storage-trace oscilloscope (BK Precision, model 2522B; Placentia, Calif.). Sham-injured animals underwent identical surgical procedures but did not receive an impact injury. Appropriate pre- and post-injury management was maintained.

Preparation of Cortical Tissue and CSF
CSF and brain cortices were collected from animals at various intervals after sham-injury or TBI. At the appropriate time-points, TBI or sham-injured animals were anesthetized as described above and secured in a stereotactic frame with the head allowed to move freely along the longitudinal axis. The head was flexed so that the external occipital protuberance in the neck was prominent and a dorsal midline incision was made over the cervical vertebrae and occiput. The atlanto-occipital membrane was exposed by blunt dissection and a 25G needle attached to polyethylene tubing was carefully lowered into the cisterna magna. Approximately 0.1 to 0.15 ml of CSF was collected from each rat. Following CSF collection, animals were removed from the stereotactic frame and immediately killed by decapitation.

Ipsilateral and contralateral (to the impact site) cortices were then rapidly dissected, rinsed in ice cold PBS, and snap frozen in liquid nitrogen. Cortices beneath the craniotomies were excised to the level of the white matter and extended ~4 mm laterally and ~7 mm rostrocaudally. CSF samples were centrifuged at 4000 g for 4 min. at 4° C. to clear any contaminating erythrocytes. Cleared CSF and frozen tissue samples were stored at −80° C. until ready for use. Cortices were homogenized in a glass tube with a TEFLON dounce pestle in 15 volumes of an ice-cold triple detergent lysis buffer (20 mM Hepes, 1 mM EDTA, 2 mM EGTA, 150 mM NaCl, 0.1% SDS, 1.0% IGEPAL 40, 0.5% deoxycholic acid, pH 7.5) containing a broad range protease inhibitor cocktail (Roche Molecular Biochemicals, cat. #1-836-145).

Human CSF samples were obtained with informed consent from human subjects suffering from TBI, and from control patients without TBI, having hydrocephaly.

Sandwich ELISA.
Anti-Biomarker specific rabbit polyclonal antibody and monoclonal antibodies are produced in the laboratory. To determine reactivity and specificity of the antibodies a tissue panel is probed by Western blot. An indirect ELISA is used with the recombinant biomarker protein attached to the ELISA plate to determine the optimal concentrations of the antibodies used in the assay. This assay determines a robust concentration of anti-biomarker to use in the assay. 96-well microplate wells are coated with 50 ng/well and the rabbit and mouse anti-biomarker antibodies are diluted serially starting with a 1:250 dilution down to 1:10,000 to determine the optimum concentration to use for the assay. A secondary anti-rabbit (or mouse)-horseradish peroxidase (HRP) labeled detection antibody and Ultra-TMB are used as detection substrate to evaluate the results.

Once the concentration of antibody for maximum signal are determined, maximum detection limit of the indirect ELISA for each antibody is determined. 96-well microplates are coated with a concentration from 50 ng/well serially diluted to <1 pg/well. For detection antibodies are diluted to the concentration determined above. This provides a sensitivity range for the Biomarker ELISA assays and determines which antibody to chose for capture and detection antibody.

Optimization and enhancement of signal in the sandwich ELISA: The detection antibody is directly labeled with HRP to avoid any cross reactivity and to be able to enhance the signal with the amplification system, which is very sensitive. This format is used in detecting all the biomarkers. The wells of the 96-well plate are coated with saturating concentrations of purified antibody (~250 ng/well), the concentration of biomarker antigen ranges from 50 ng to <1 pg/well and the detection antibody is at the concentration determined above. Initially the complex is detected with a HRP-labeled secondary antibody to confirm the SW ELISA format, and the detection system is replaced by the HRP-labeled detection antibody.

Standard curves of biomarkers and samples from control and injured animals are used. This also determines parallelism between the serum samples and the standard curve. Serum samples are spiked with a serial dilution of each biomarker, similar to the standard curve. Parallel results are equal to 80-100% recovery. If any high concentrations of serum have interfering substances, the minimum dilution required is determined to remove the interference. The assay is used to evaluate biomarker levels in serum from injured animals having injuries of different magnitudes followed over time.

Figure 3A:
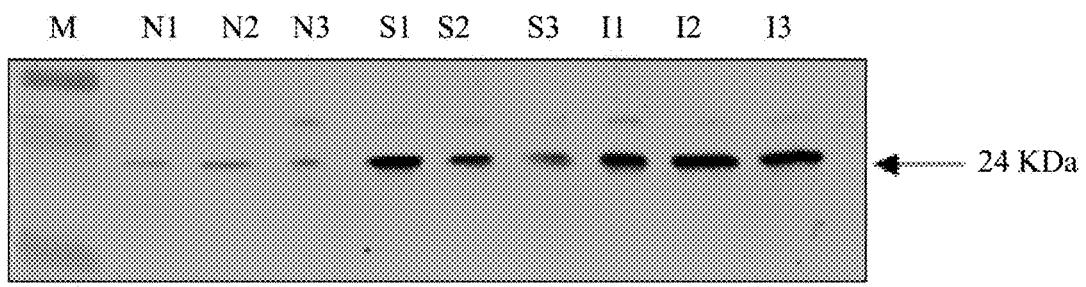
FIG. 3A is a Western Blot showing the detection and accumulation of Novel brain-specific marker #1: UCH-L1 neural protein in CSF of rodents after experimental traumatic brain injury in rats.
Figure 3B:
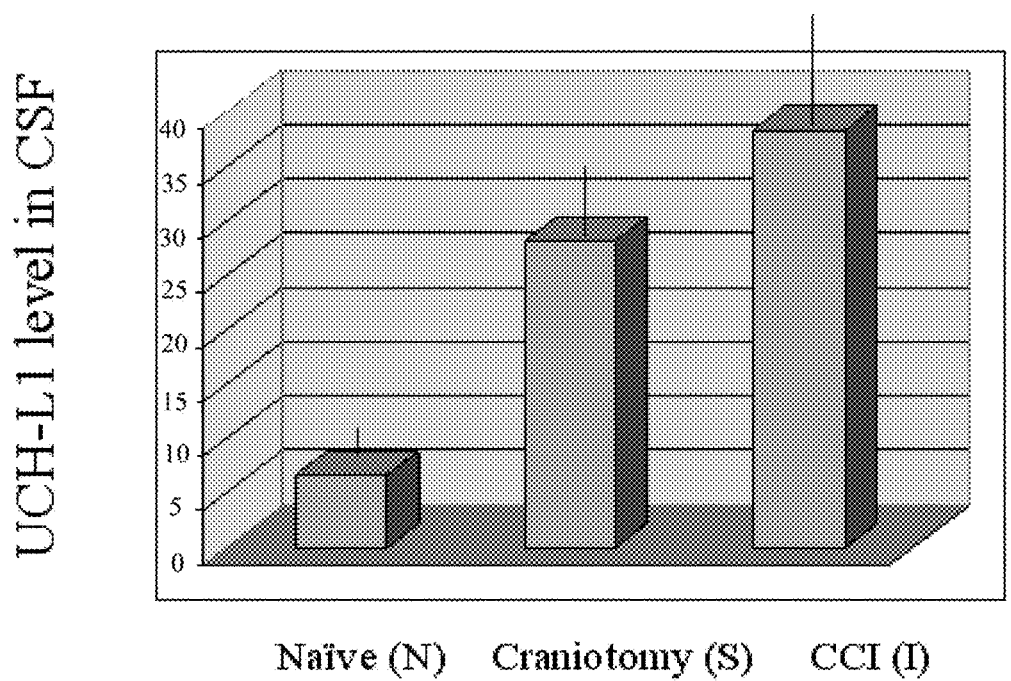
FIG. 3B is a graph showing the elevation of Novel brain-specific marker #1: Ubiquitin C-terminal hydrolase L1 (UCH-L1) in rat CSF 48 h after experimental brain injury: craniotomy and controlled cortical impact (CCI)-induced brain injury when compared to CSF from naïve control rats.
Figure 4A:
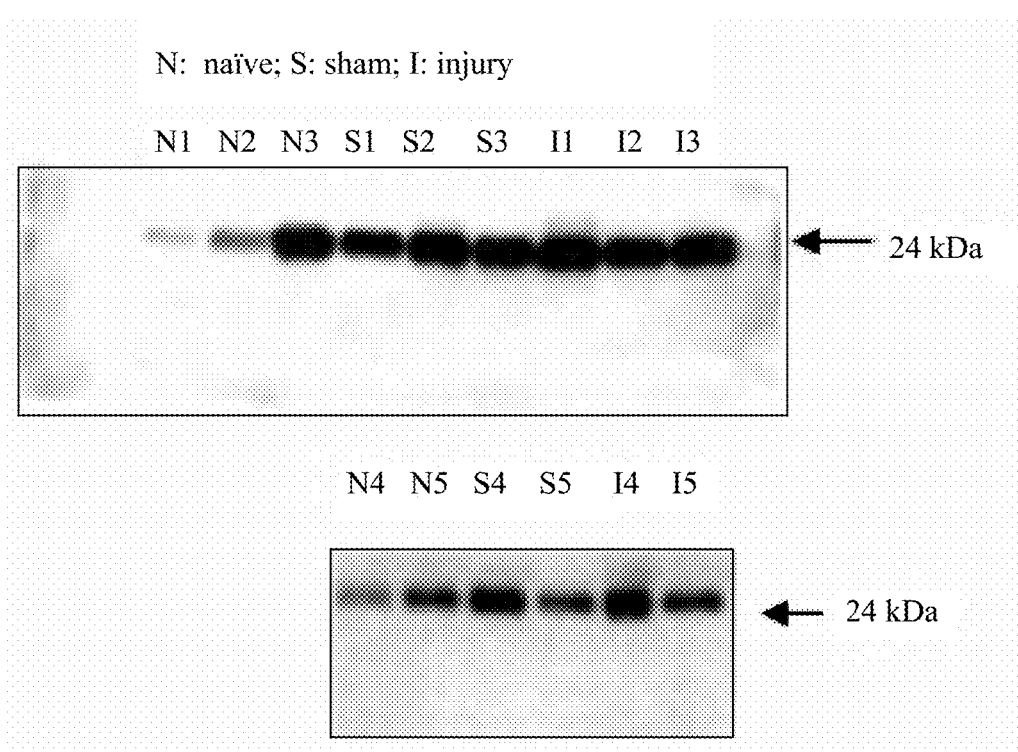
FIG. 4A is a Western Blot showing the detection and accumulation of Novel brain-specific marker #2: neuronal microtubule binding protein (p24) in CSF of rodents after experimental traumatic brain injury in rats.
Figure 4B:
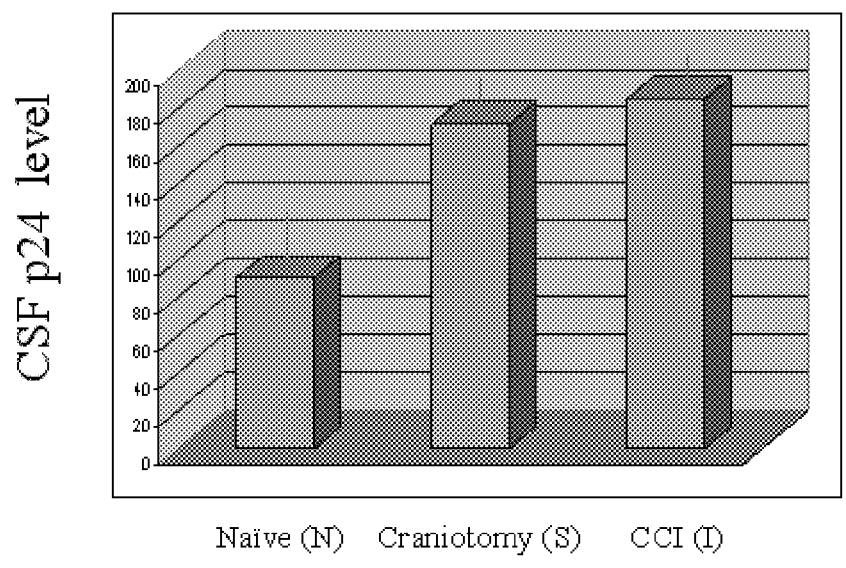
FIG. 4B is a graph showing the elevation of Novel brain-specific marker #2: neuronal microtubule binding protein (p24) in rat CSF 48 h after experimental brain injury: craniotomy and controlled cortical impact (CCI)-induced brain injury when compared to CSF from naïve control rats.

The ELISA has been developed and optimized as a standard 96-well format ELISA which is specific for the biomarkers and sensitivity in the range measured in rat and human CSF and serum. Antibodies that recognize the UCH-L1 protein with high specificity and sensitivity (FIGS. 3 and 4) were used as capture and detection antibodies. The detection antibody is labeled with horseradish peroxidase (HRP) and colorimetric development is achieved using Ultra-TMB.

Validation of UCH-L1 as a Biomarker for TBI

Figure 9A:
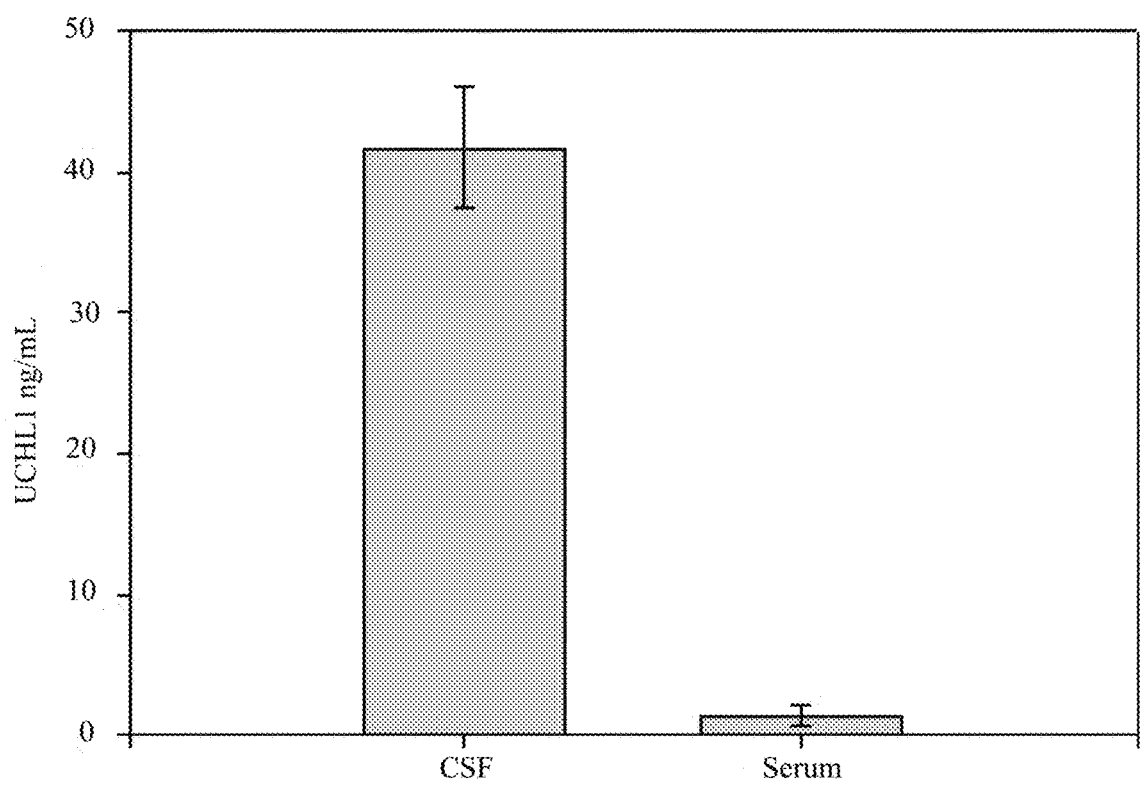
FIG. 9A is a graph showing the elevation of Novel brain-specific marker #1: Ubiquitin C-terminal hydrolase L1 (UCH-L1) as measure by quantitative sandwich ELISA with samples from human CSF and serum from patients with severe traumatic brain injury
Figure 9B:
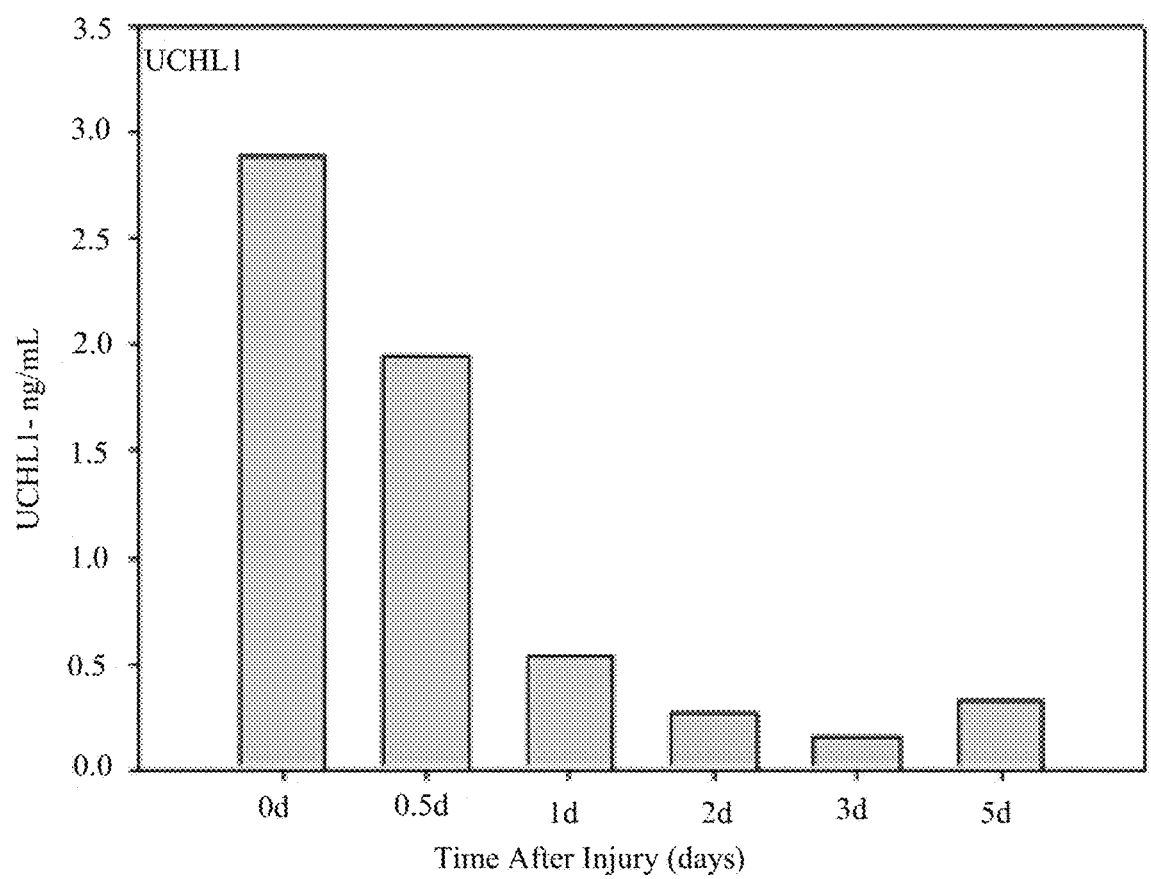
FIG. 9B is a graph showing the temporal changes measured by quantitative sandwich ELISA in levels of UCH-L1 measured in serum for a patient with severe TBI. Serum samples were taken at the time the patient was admitted to the hospital (0d), and at 12 hours (1d), 48 hours (2d), 72 hours (3d), and 120 hours (5d) after the time of injury.

Using rat and human samples obtained from the University of Florida (Gainesville, Fla. and Banyan Biomarkers, Alachua Fla.) has confirmed that UCH-L1 is a reliable and sensitive biomarker for TBI. Rat CSF and serum samples were obtained from animals that had received an experimental brain injury using controlled cortical impact. UCH-L1 levels in CSF and serum (FIG. 9) were significantly higher in brain injured animals than they were in uninjured or sham-injured controls. Likewise, high levels of UCH-L1 can be measured in serum from human patients with brain injuries but are below the level of assay detection in normal healthy people (FIG. 9).

Gel Electrophoresis and Immunoblot Analyses of CSF

Protein concentrations of CSF were determined by bicinchoninic acid microprotein assays (Pierce Inc., Rockford, Ill.) with albumin standards. Protein balanced samples were prepared for sodium dodecyl sulfate-polyacrylamide gel electrophoresis (SDS-PAGE) in twofold loading buffer containing 0.25 M Tris (pH 6.8), 0.2 M DTT, 8% SDS, 0.02% bromophenol blue, and 20% glycerol in distilled $H_2O$. Samples were heated for 2 min. at 90° C. and centrifuged for 1 min. at 10,000 rpm in a microcentrifuge at ambient temperature. Twenty to forty micrograms of protein per lane was routinely resolved by SDS-PAGE on 6.5% Tris/glycine gels for 1 hour at 200V. Following electrophoresis, separated proteins were laterally transferred to polyvinylidene fluoride (PVDF) membranes in a transfer buffer containing 400 mM glycine and 0.025 M Tris (pH 8.9) with 5% methanol at a constant voltage of 125 V for 2 hour at 4° C. Blots were blocked for 1 hour at ambient temperature in 5% nonfat milk in TBST (25 mM TrisHCl pH 7.4, 150 mM NaCl, 0.05% Tween-20, 0.02% sodium azide).

Immunoblots containing brain or CSF protein were probed with an anti-neural protein specific primary antibodies (e.g. anti-UCH-L1, anti-alpha-synuclein and anti-p24). Following an overnight incubation at 4° C. with the primary antibodies in 5% nonfat milk in TBST, blots were incubated for 1 hour at ambient temperature in 5% nonfat milk that contained an alkaline phosphatase or horseradish peroxidase-conjugated goat anti-mouse IgG (1:10,000 dilution) or goat-anti-rabbit IgG (1:3000). Alkaline phosphatase-based colorimetric development (BCIP-NBT substrate) or enhanced chemiluminescence (ECL, Amersham) reagents were used to visualize immunolabeling on Kodak Biomax ML chemiluminescent film.

Assessing Neural Protein Release

SDS-Polyacrylamide (SDS-PAGE) gel electrophoresis and immunoblotting. At the end of an experiment, cells were harvested from 5 identical culture wells and collected in 15 ml centrifuge tubes and centrifuged at 3000 g for 5 min. The medium was removed and the pellet cells were rinsed with 1×DPBS. Cells were lysed in ice cold homogenization buffer [20 mM PIPES (pH 7.6), 1 mM EDTA, 2 mM EGTA, 1 mM DTT, 0.5 mM PMSF, 50 pg/mL Leupeptin, and 10 pg/mL each of AEBSF, aprotinin, pepstatin, TLCK and TPCK for 30 min., and sheared through a 1.0 mL syringe with a 25 gauge needle 15 times. Protein content in the samples was assayed by the Micro BCA method (Pierce, Rockford, Ill., USA).

For protein electrophoresis, equal amounts of total protein (30 µg) were prepared in two fold loading buffer containing 0.25 M Tris (pH6.8), 0.2 M DTT, 8% SDS, 0.02% bromophenol blue, and 20% glycerol, and heated at 95° C. for 10 min. Samples were resolved in a vertical electrophoresis chamber using a 4% stacking gel over a 7% acrylamide resolving gel for 1 hour at 200V. For immunoblotting, separated proteins were laterally transferred to nitrocellulose membranes (0.45 µM) using a transfer buffer consisting of 0.192 M glycine and 0.025 M Tris (pH 8.3) with 10% methanol at a constant voltage (100 V) for 1 hour at 4° C. Blots were blocked overnight in 5% non-fat milk in 20 mM Tris, 0.15 M NaCl, and 0.005% Tween-20 at 4° C. Coomassie blue and Panceau red (Sigma, St. Louis, Mo.) were used to stain gels and nitrocellulose membranes (respectively) to confirm that equal amounts of protein were loaded in each lane.

Immunoblots were probed as described below with a primary antibody (e.g. anti-UCH-L1 monoclonal antibody raised in mouse (Chemicon), anti-alpha-synuclein monoclonal antibody raised in mouse (Chemicon), anti-p24 monoclonal antibody raised in mouse (Becton Dickson Bioscience). Following incubation with the primary antibody (1:2000) for 2 hours at room temperature, the blots were incubated in peroxidase-conjugated sheep anti-mouse IgG for 1 hour (1:10,000). Enhanced chemiluminescence reagents (ECL, Amersham) were used to visualize the immunolabeling on Hyperfilm (Hyperfilm ECL, Amersham).

Statistical Analyses.

Quantitative evaluation of protein levels detected by immunoblotting was performed by computer-assisted densitometric scanning (ImageJ-NIH). Data were acquired as integrated densitometric values and transformed to percentages of the densitometric levels obtained on scans from sham-injured animals visualized on the same blot. Data was evaluated by least squares linear regression followed by ANOVA. All values are given as mean±SEM. Differences were considered significant if p<0.05.

Figure 5A:
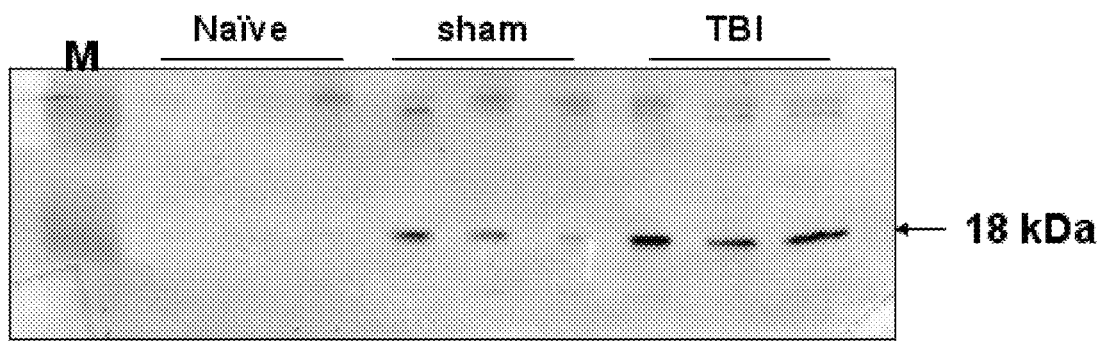
FIG. 5A is a Western Blot showing the detection and accumulation of Novel brain-specific marker #3: Neuronal protein α-synuclein in CSF of rodents after experimental traumatic brain injury in rats.
Figure 5B:
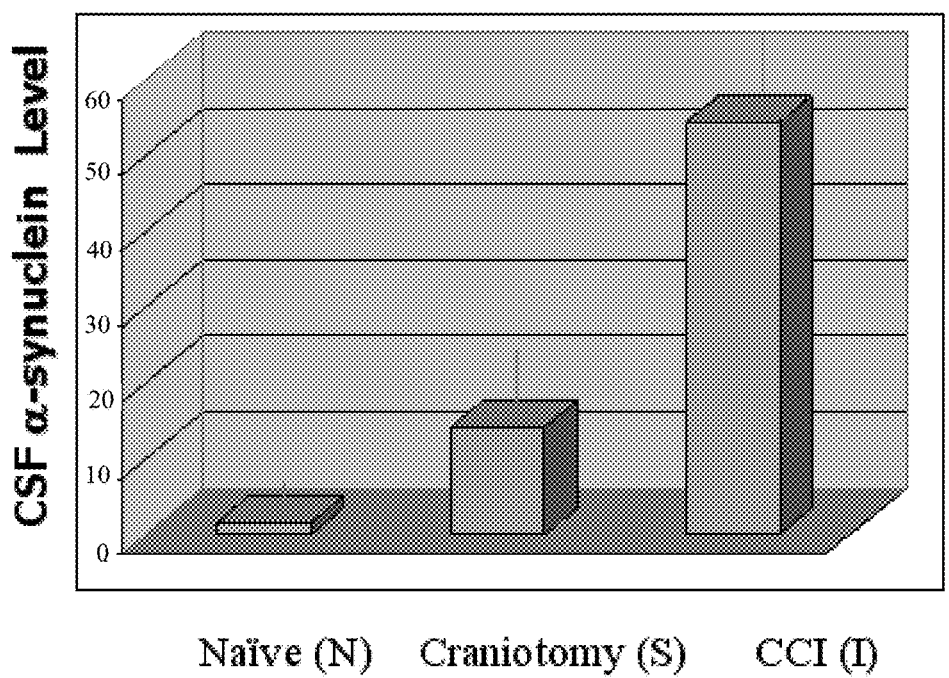
FIG. 5B is a graph showing the elevation of Novel brain-specific marker #3: Neuronal protein α-synuclein in rat CSF 48 h after experimental brain injury: craniotomy and controlled cortical impact (CCI)-induced brain injury when compared to CSF from naïve control rats.

Example 1: Detection of Neural Proteins UCH-L1, p24, and Alpha-Synuclein in CSF of Rodents Following TBI TBI was induced in rodents as described above. Following TBI or sham operation or naïve rats, samples of CSF were collected and analyzed for presence of three novel neural protein biomarkers (e.g. UCH-L1 (FIG. 3), p24 (FIG. 4) and alpha-synuclein (FIG. 5). Results, shown in FIGS. 3-5, demonstrated independent or concurrent accumulation of UCH-L1 (see FIG. 3), p24 (see FIG. 4) and alpha-synuclein (see FIG. 5), in the CSF of rodents after TBI. Significantly less of these neural proteins were observed in sham-injured and naïve controls. Each lane in the blots represents a different animal. The sensitivity of this assay permits detection of inter-animal differences, which is valuable for prediction of outcome. The results of this study demonstrated that after TBI, neural proteins accumulated in the CSF in sufficient levels to be easily detectable on Western blots or by other immunoassays such as ELISA.

Example 2: Detection of Neural Proteins UCH-L1 and p24 in CSF of Human TBI

Figure 6A:
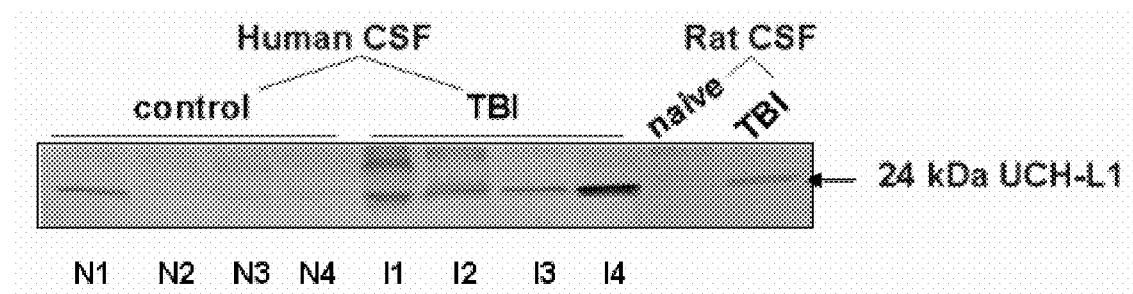
FIG. 6A is a Western Blot showing the detection and accumulation of Neuronal biomarker #1 UCH-L1 levels are elevated in human CSF 24 h after TBI.
Figure 6B:
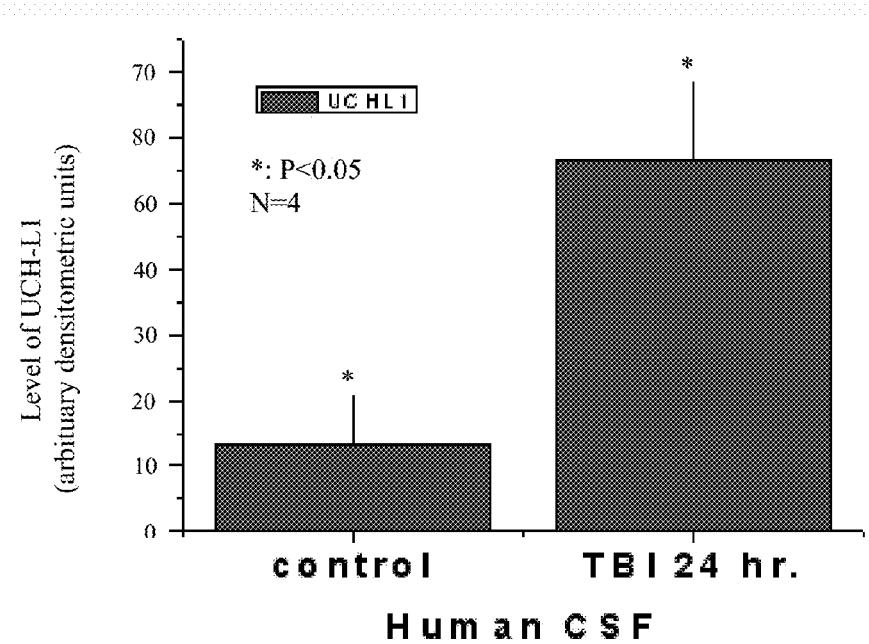
FIG. 6B is a graph showing the elevation of Neuronal biomarker #1 UCH-L1 levels are elevated in human CSF 24 h after traumatic brain injury, when compared to CSF from neurological controls with no apparent brain injury.
Figure 7A:
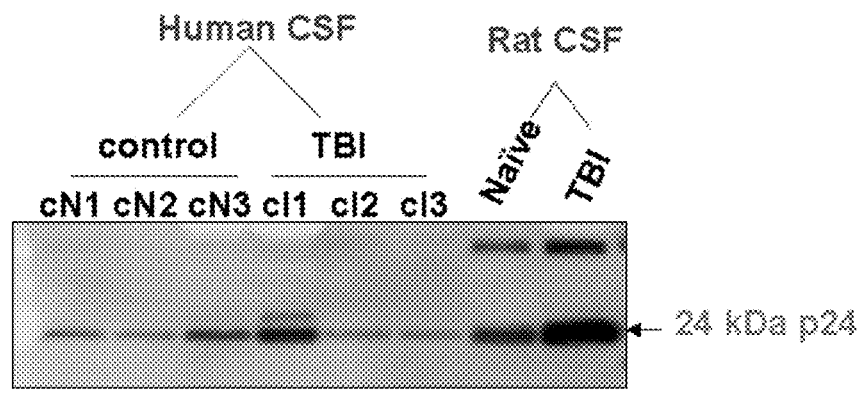
FIG. 7A is a Western Blot showing the detection and accumulation of Novel brain-specific marker #2: neuronal microtubule binding protein (p24) in human CSF after traumatic brain injury
Figure 7B:
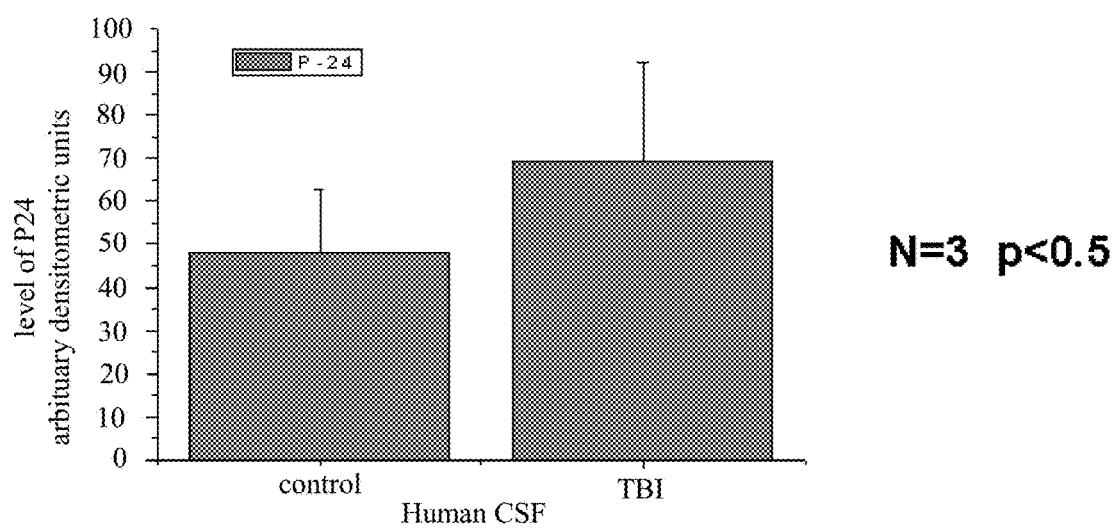
FIG. 7B is a graph showing the elevation of Neuronal biomarker Novel brain-specific marker #2: neuronal microtubule binding protein (p24) in human CSF 24 h after traumatic brain injury when compared to CSF from neurological controls with no apparent brain injury.
Figure 8A:
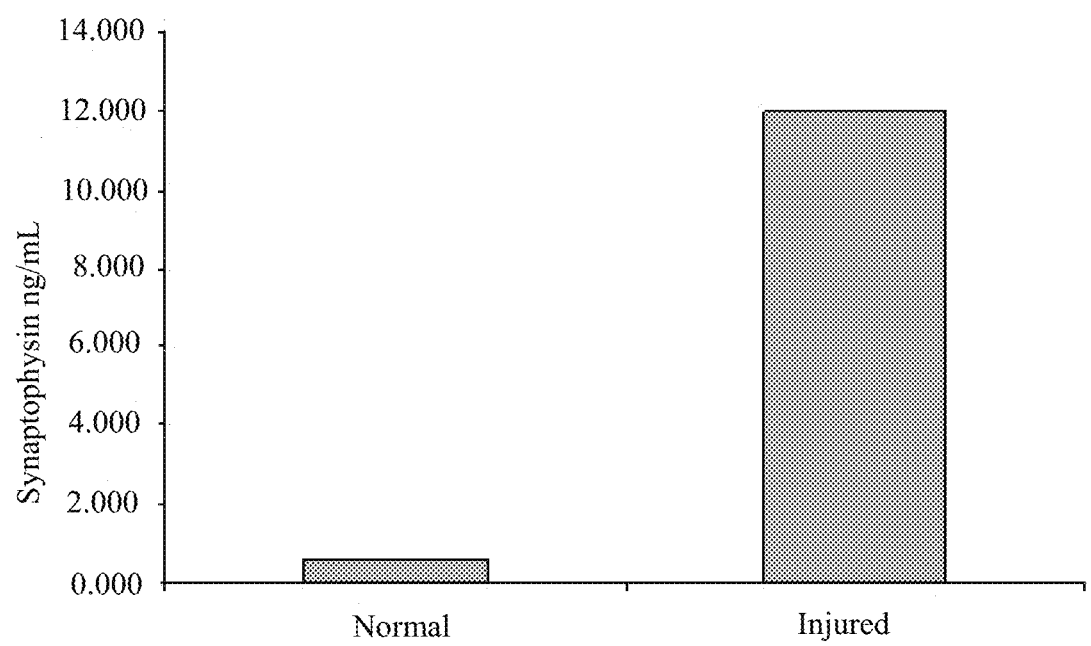
FIG. 8A are the results from a quantitative SW ELISA for synaptophysin showing the detection of Novel brain-specific marker #4: synaptophysin in rat CSF after traumatic brain injury when compared to CSF from neurological controls with no apparent brain injury.
Figure 8B:
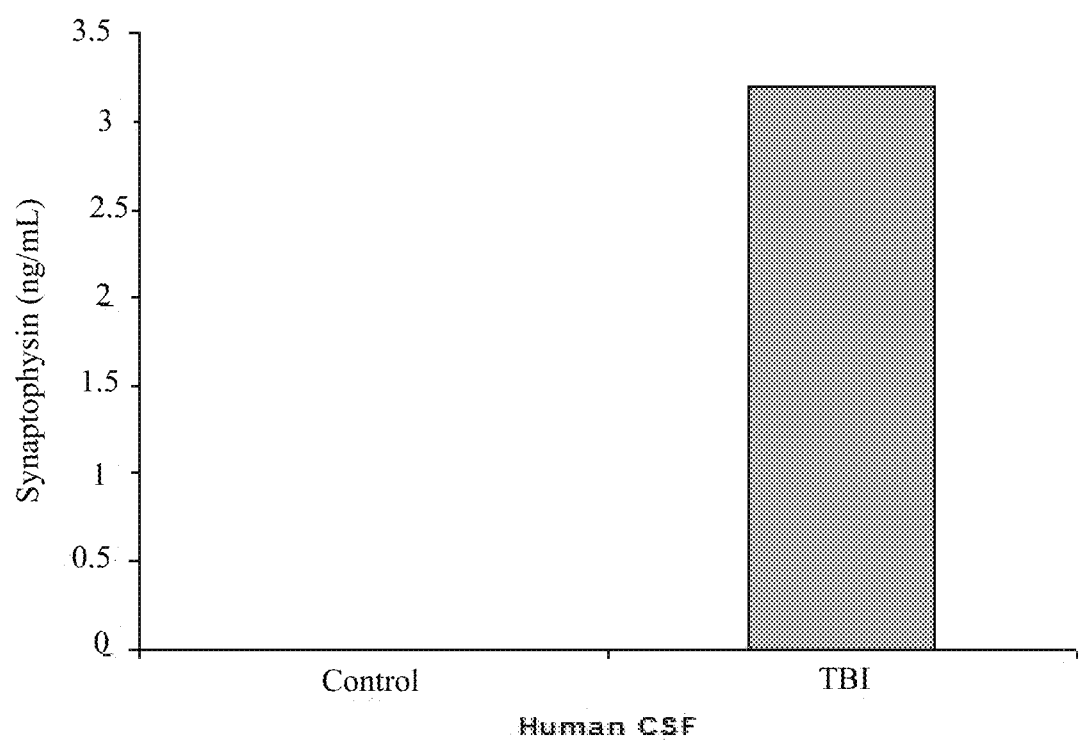
FIG. 8B is a graph showing the elevation of Neuronal biomarker Novel brain-specific marker #2: neuronal microtubule binding protein (p24) in human CSF 24 h after traumatic brain injury when compared to CSF from neurological controls with no apparent brain injury.

Accumulation of novel neural markers (UCH-L1 and p24) was analyzed in samples of human CSF taken at 24 hr after TBI. From five patients who experienced severe TBI and five neurological controls (normal pressure hydrocephalus. As in the rodent models of TBI, the neural proteins examined (UCH-L1 and p24) were prominent in CSF samples TBI. Levels of these neural proteins were much higher in the TBI patients than in the control patients (e.g. UCH-L1 (FIG. 6), p24 (FIG. 7). These data demonstrated that after TBI, neural proteins accumulated in human CSF in sufficient levels to be easily detectable on Western blots or by other immunoassays such as ELISA.

Figure 10A:
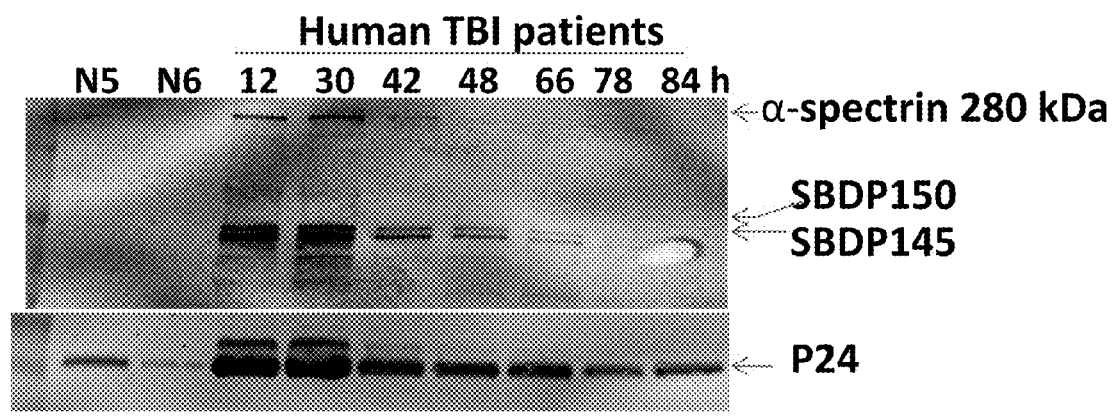
FIG. 10A is a Western Blot showing detection and accumulation of neurensin (p24) in cerebral spinal fluid (CSF) in human patients with brain injury showing p24 accumulation and spectrin breakdown product (SPDP) 150 kDa and 145 kDa measured at 12, 30, 42, 48, 66, 78 and 84 hours after injury compared to controls N5 and N6.
Figure 10B:
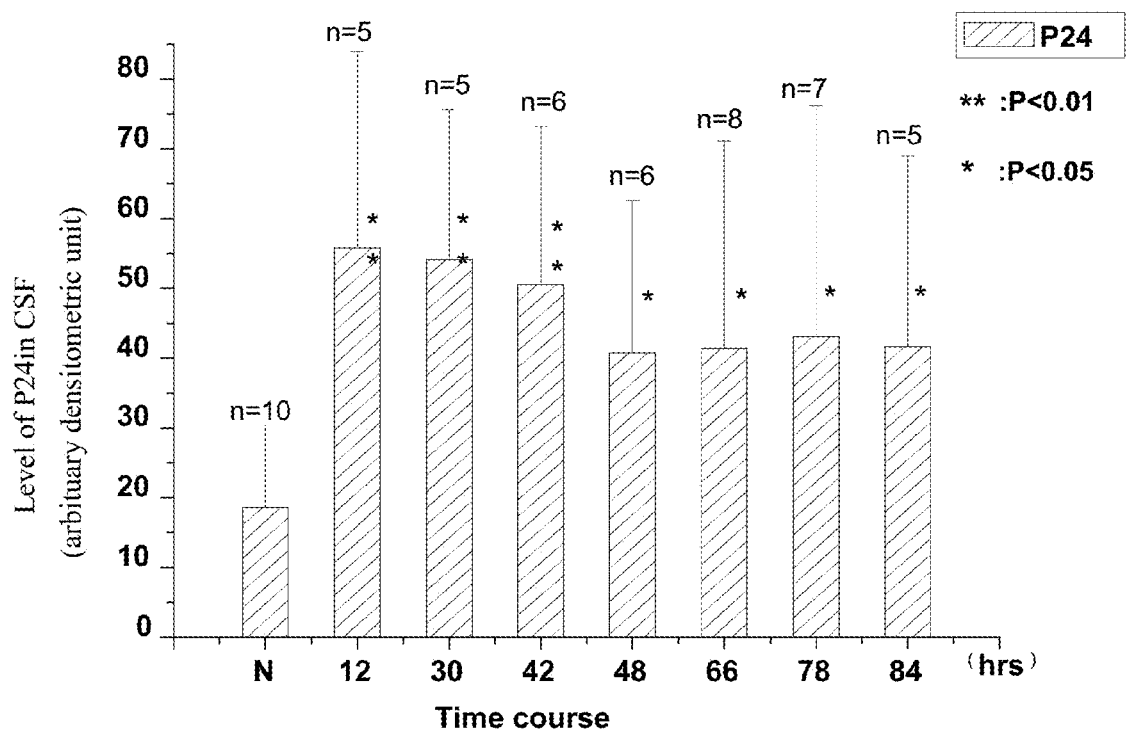
FIG. 10B is a graph showing densiometric quantification of CSF p24 levels in CSF in human brain injured patients at 12, 30, 42, 48, 66, 78 and 84 hours after injury compared to a control N.

Example 3 shows that standard immunodetection method can be used to detect and quantify P24/Neurorensin biomarker elevation in Human TBI patient CSF versus control CSF. FIG. 10A shows immunoblotting detection of P24 and SBDP biomarker in human TBI patient CSF (12, 30, 42, 48, 78 and 84 h after injury) versus controls (N) and FIG. 10B shows densitometric quantification of CSF P24 levels are demonstrated.

Figure 11A:
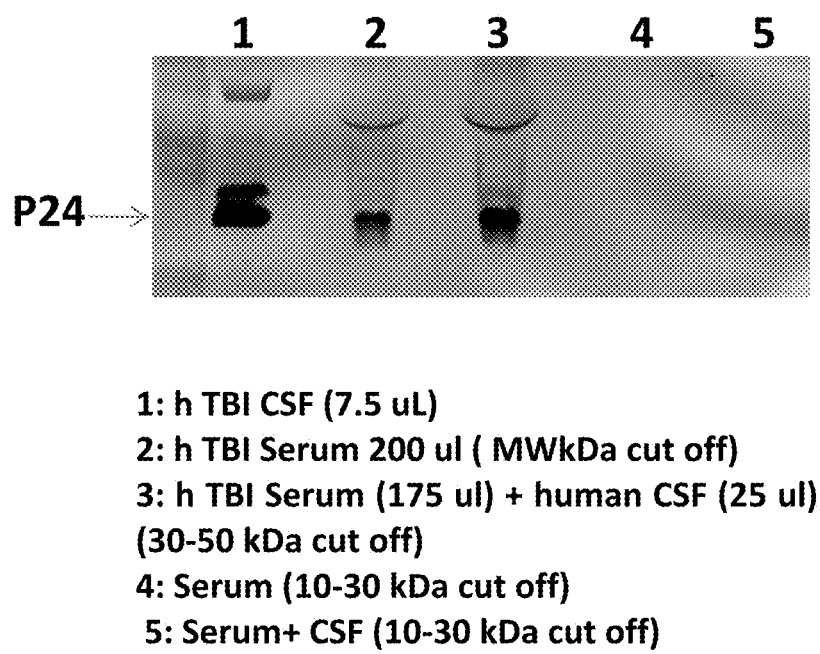
FIG. 11A is a Western Blot showing neurensin (p24) biomarker immunoblotting detection in human serum using a centrifuging filtration/concentration technique in molecular weight range of 30-50 kDa fraction at 24 hours after injury; 1 shows human TBI CSF (7.5 ul); 2 is human TBI serum (200 ul with MW kDa cutoff); 3 is human TBI serum (175 ul plus human 25 ul CSF); 4 is serum (10-30 kDa cut off); 5 is serum plus CSF (10-30 kDa cut off).
Figure 11B:
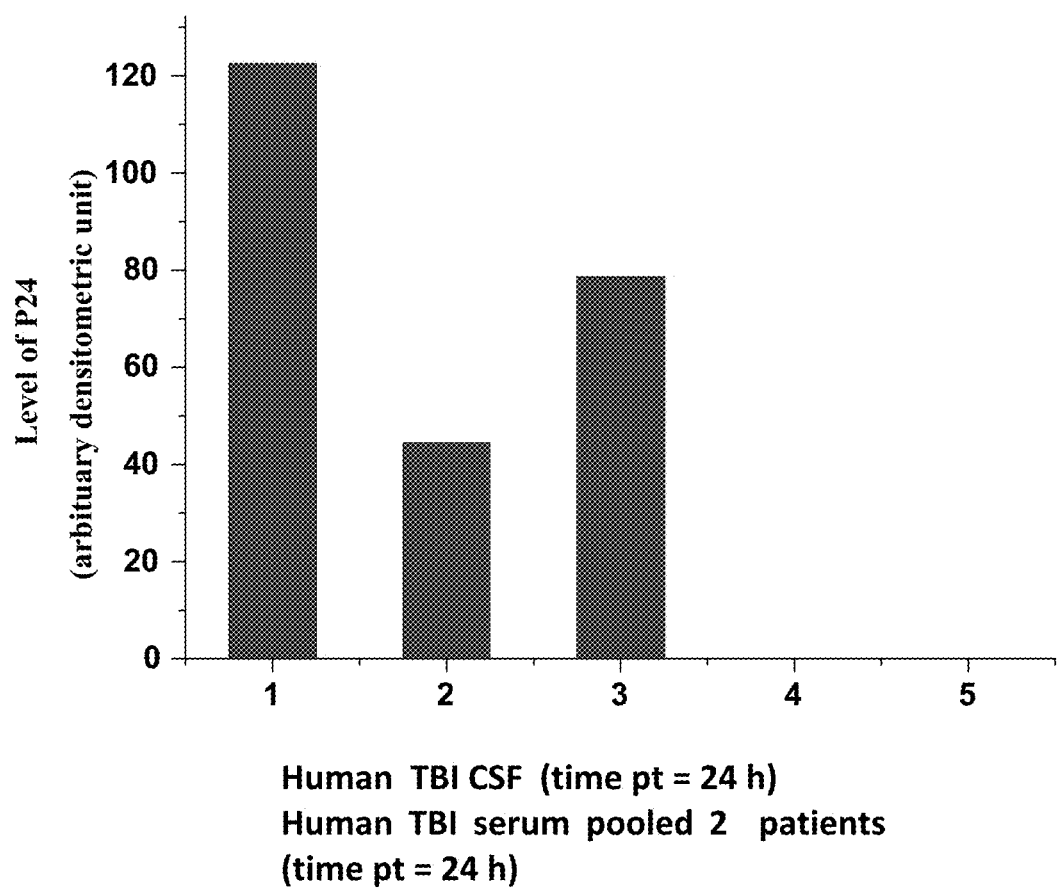
FIG. 11B is a graph showing densiometric quantification of serum p24 levels. The same method applied to normal control serum samples showed no detection of p24 levels (level=0; data not shown). Serum was pooled from 2 human patients.

Example 4 shows that standard immunodetection method can also be used to detect and quantify P24/Neurorensin biomarker detection in Human TBI patient Serum. FIG. 11A shows immunoblotting detection of P24 in human TBI serum using sequential centrifuging filtration/concentration units (1.5 mL) and technique in molecular weight rang of 30-50 kDa fraction, and FIG. 11B shows densitometric quantification of serum P24 levels is demonstrated. Same method applied to normal control serum samples show no detection of P24 (level=zero; data not shown).

Figure 12A:
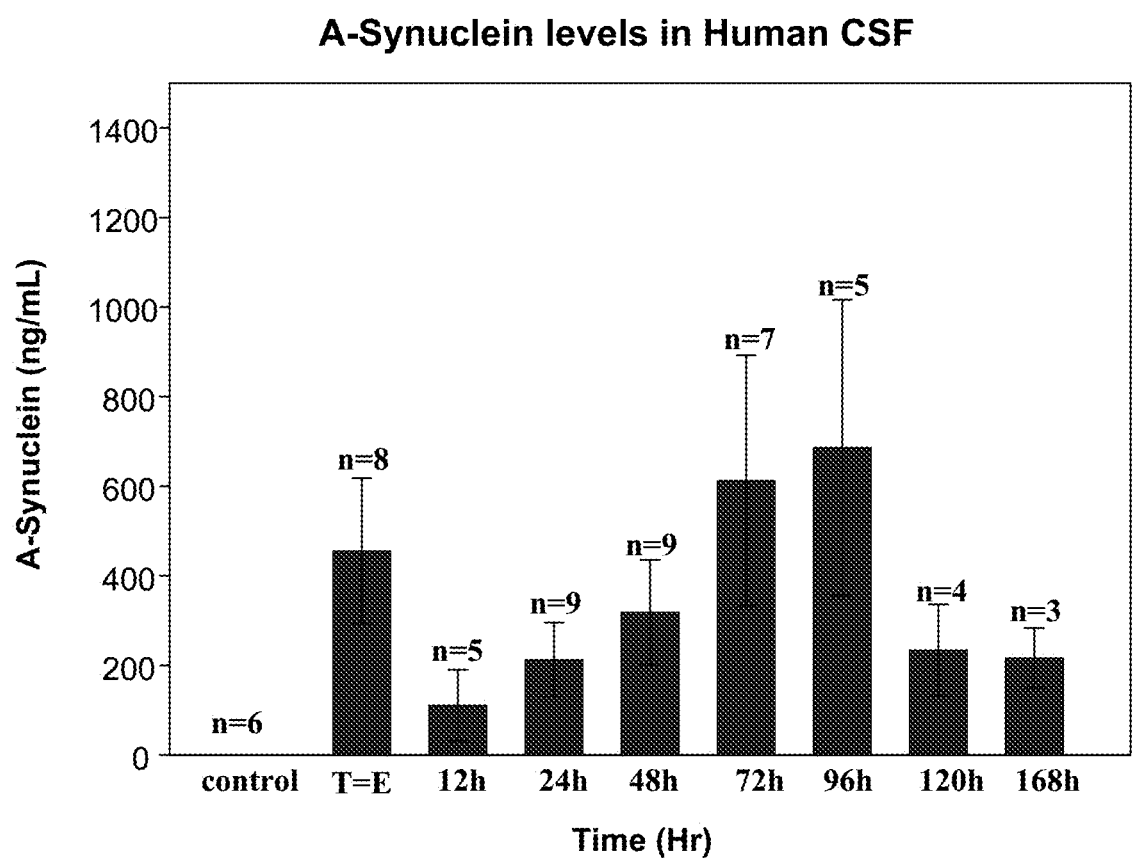
FIG. 12A is a graph showing alpha-synuclein biomarker elevation in human TBI patient CSF detected by sandwich ELISA. Alpha-synuclein levels in control non-brain injured CSF were compared to TBI patient CSF samples collected at different post injury time (T=enrollment) or 12, 24, 48, 72, 96, 120 and 168 hours after injury.
Figure 12B:
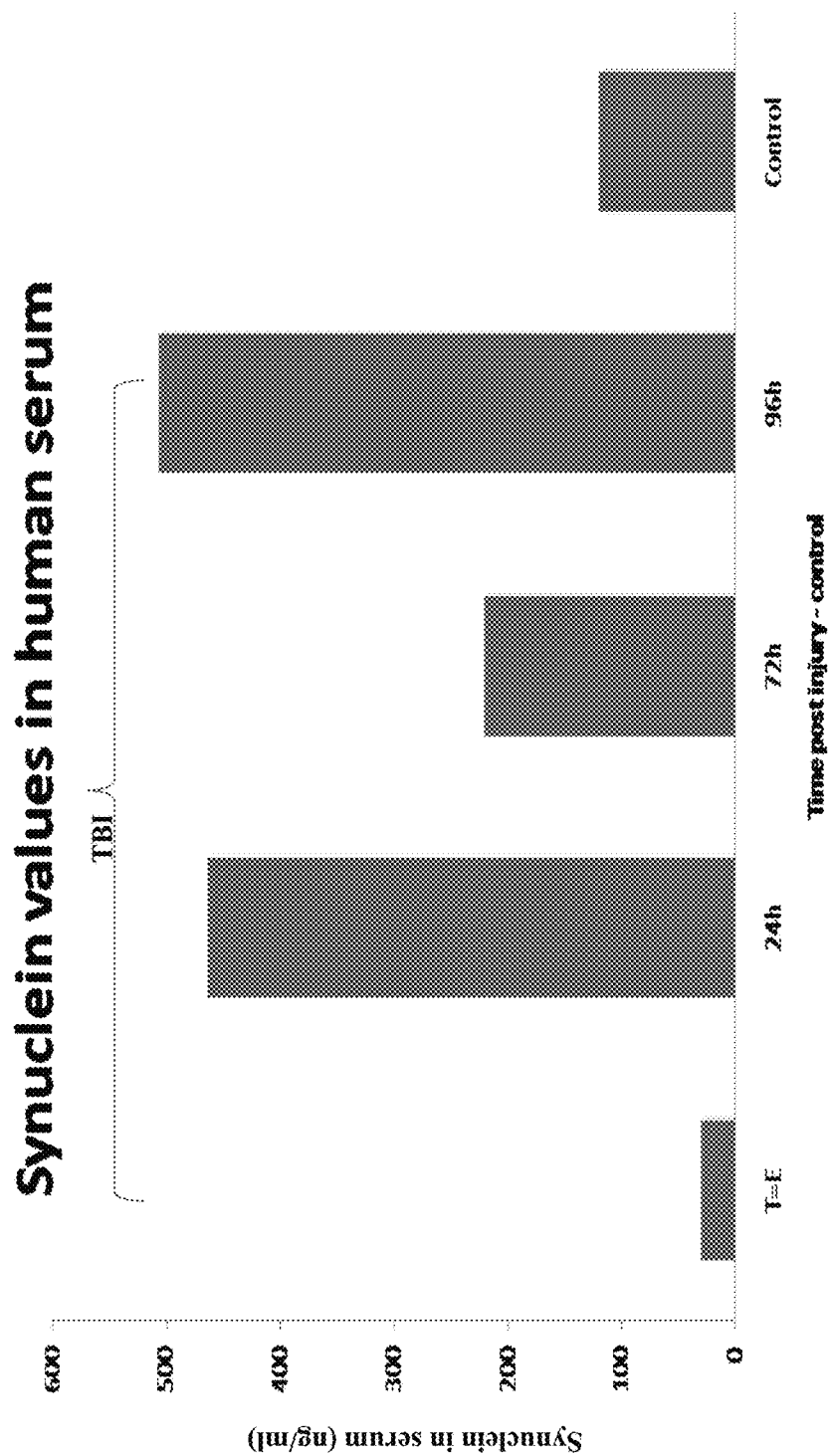
FIG. 12B is a graph showing alpha-synuclein levels in normal control (non-brain injured) serum compared to TBI patient serum samples collected at different post-injury times (T=E (enrollment) or 24, 72 and 96 hr after injury and showed significant elevation compared to control serum from uninjured patients.

Example 5 shows that standard immunodetection method (ELISA) can also be used to detect and quantify alpha-synuclein biomarker elevation in human TBI patient CSF (FIG. 12A) and serum (FIG. 12B). Sandwich ELISA based detection of alpha-synuclein was used. In FIG. 12A, alpha-synuclein levels in control non-brain injured CSF were compared to TBI patient CSF samples collected at different post-injured time (T=E (enrollment) or 12, 24, 48, 72, 96, 120 and 168 h after injury. In FIG. 12B, alpha-synuclein levels in normal control (non-brain injured) serum were compared to TBI patient serum samples collected at different post-injured time (T=E (enrollment) or 24, 72, 96 h after injury).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method for detecting Glial Fibrillary Acidic Protein (GFAP), comprising:
   detecting whether GFAP is present in a biological sample collected from a subject suspected of having a concussion by contacting the biological sample with an anti-GFAP antibody and detecting binding of the antibody to GFAP, wherein said biological sample is a blood, blood plasma, or serum sample, wherein the concussion is induced by a traumatic insult.

2. The method of claim 1, further comprising detecting ubiquitin C-terminal hydrolase L1 (UCH-L1) in the sample by contacting the sample with an anti-UCH-L1 antibody and detecting binding between the UCH-L1 and the antibody.

3. The method of claim 1, wherein the traumatic insult is a blow to the head, a gunshot wound, an automobile accident, a sport accident or shaken baby syndrome.

4. The method of claim 1, wherein said biological sample is serum.

5. The method of claim 1, wherein said GFAP is detected using an immunoassay.

6. The method of claim 5, wherein the immunoassay is an ELISA or a sandwich assay.

7. A method for detecting Glial Fibrillary Acidic Protein (GFAP), comprising:
   detecting whether GFAP is present in a biological sample collected from a subject suspected of having a concussion by contacting the biological sample with an anti-GFAP antibody and detecting binding of the antibody to GFAP, wherein said biological sample is a blood, blood plasma, or serum sample, wherein the subject is not suspected of having a stroke.

8. The method of claim 7, further comprising detecting ubiquitin C-terminal hydrolase L1 (UCH-L1) in the sample by contacting the sample with an anti-UCH-L1 antibody and detecting binding between the UCH-L1 and the antibody.

9. The method of claim 7, wherein said GFAP is detected using an immunoassay.

10. The method of claim 9, wherein the immunoassay is an ELISA or a sandwich assay.

11. A method for detecting Glial Fibrillary Acidic Protein (GFAP), comprising:
    detecting whether GFAP is present in a biological sample collected from a subject suspected of having a concussion by contacting the biological sample with an anti-GFAP antibody and detecting binding of the antibody to GFAP, wherein said biological sample is a blood, blood plasma, or serum sample, wherein the subject is not suspected of having:
    reduced blood flow or ischemia that results in deficient blood supply and death of tissues in one area of the brain; or sudden diminution or loss of consciousness, sensation, and voluntary motion caused by rupture or obstruction of an artery of the brain.

12. The method of claim 11, further comprising detecting ubiquitin C-terminal hydrolase L1 (UCH-L1) in the sample by contacting the sample with an anti-UCH-L1 antibody and detecting binding between the UCH-L1 and the antibody.

13. The method of claim 11, wherein said GFAP is detected using an immunoassay.

14. The method of claim 13, wherein the immunoassay is an ELISA or a sandwich assay.

* * * * *